United States Patent [19]

Tom

[11] Patent Number: 5,583,282
[45] Date of Patent: Dec. 10, 1996

[54] DIFFERENTIAL GAS SENSING IN-LINE MONITORING SYSTEM

[75] Inventor: Glenn M. Tom, New Milford, Conn.

[73] Assignee: Millipore Investment Holdings Limited, Wilmington, Del.

[21] Appl. No.: 270,171

[22] Filed: Jul. 1, 1994

Related U.S. Application Data

[63] Continuation-in-part of Ser. No. 930,184, Aug. 17, 1992, Pat. No. 5,325,705, which is a continuation-in-part of Ser. No. 628,490, Dec. 14, 1990, Pat. No. 5,138,869.

[51] Int. Cl.$^6$ ................................................. G01N 27/00
[52] U.S. Cl. ............................................. 73/31.03; 73/1 G
[58] Field of Search ........................ 73/1 G, 23.2, 23.21, 73/23.23, 29.02, 31.03, 31.02; 422/88, 93

[56] References Cited

U.S. PATENT DOCUMENTS

| | | | |
|---|---|---|---|
| 2,889,701 | 6/1959 | Skarstrom | 73/23.2 |
| 4,254,654 | 3/1981 | Clouser et al. | 73/23.4 |
| 4,312,228 | 1/1982 | Wohltjen | 73/23.31 X |
| 4,316,382 | 2/1982 | Woodruff | 73/23.2 |
| 4,960,568 | 10/1990 | Matsumoto et al. | 422/83 |
| 5,027,642 | 7/1991 | Wen et al. | 73/23.2 |
| 5,138,869 | 8/1992 | Tom | 73/31.03 |
| 5,223,783 | 6/1993 | Wilis | 73/23.2 X |
| 5,305,630 | 4/1994 | Molozay et al. | 73/31.03 X |
| 5,325,705 | 7/1994 | Tom | 73/31.03 |

OTHER PUBLICATIONS

System 3A Hygrometer, Panametrics, Ltd. (Shannon, Ireland) Dec., 1988.
System 580 Hygrometer, Panametrics, Ltd. (Shannon, Ireland), Aug. 1989.
Product Literature for DuPont 5700 Moisture Analyzer (E. I. DuPont De Nemours & Co., Wilmington, DE), Jan. 1987.
System 1/O$_2$ Microprocessor–Based Moisture and Oxygen Content Analyzer, Panametrics, Ltd. (Shannon, Ireland), Mar., 1990.
M Series/Aluminum Oxide Moisture Sensor for Gases and Liquids, Panametrics, Ltd. (Shannon, Ireland), Feb., 1990.

*Primary Examiner*—Michael J. Brock
*Attorney, Agent, or Firm*—Steven J. Hultquist

[57] ABSTRACT

An in-line detector system and method for real-time detection of impurity concentration in a flowing gas stream. In a specific aspect, the system may comprise an in-line monitoring system for determining the calibrated concentration of an impurity species in a flowing gas stream, in a low concentration range below a predetermined concentration value, and in a high concentration range above said predetermined concentration value. The system may utilize hygrometric sensors in the case of water as a critical impurity, or surface acoustical wave (SAW) devices coated with suitable impurity-affinity coatings. The method includes sensing the impurity species concentration in gas derived from the gas flow stream in a sequential and repetitive sensing operation. In a first sensing mode the gas is purified of impurity species prior to sensing thereof and in a second sensing mode the gas is unpurified. In the first sensing mode and second sensing mode, the cycle times are varied in accordance with the impurity species concentration. In the low concentration range the second sensing mode cycle time is longer than the first sensing mode cycle time and in the high concentration the first sensing mode cycle time is longer than the second sensing mode cycle time.

22 Claims, 8 Drawing Sheets

1

DIFFERENTIAL GAS SENSING IN-LINE MONITORING SYSTEM

This application is a continuation-in-part of prior U.S. patent application Ser. No. 07/930,184 filed Aug. 17, 1992 in the name of Glenn M. Tom, to issue Jul. 5, 1994 as U.S. Pat. No. 5,325,705, which in turn was a continuation-in-part of U.S. patent application Ser. No. 07/628,490, filed Dec. 14, 1990 in the name of Glenn M. Tom, and issued Aug. 18, 1992 as U.S. Pat. No. 5,138,869.

BACKGROUND OF THE INVENTION

1. Field of the Invention

This invention relates to means and method for detecting the calibrated concentration of an impurity species in a flowing gas stream, in a low concentration range, and in a high concentration range, with rapid recovery to normal operation after exposure to high concentrations of impurity.

2. Description of the Related Art

The rapid expansion of vapor-phase processing techniques, e.g., chemical vapor deposition, in the semiconductor industry has been associated with the deployment and use of manufacturing equipment which is totally reliant on the delivery of ultra-high purity process gases at the point of use in the semiconductor manufacturing facility. Currently, over 5 billion dollars worth of such equipment is in use.

Despite the widespread commercial employment of such vapor-phase processing equipment, little effort has been focused to date on the development of systems for monitoring purity of gas streams in the process system.

As a result of the absence of commercially suitable gas impurity monitoring systems, there is a recurrence of circumstances where a large number of wafers have been processed in the vapor-phase deposition reactor before it is recognized that compositional changes in the process gas stream flowed to the reactor are leading to high rates of rejection. Such high rates of rejection in turn significantly lower the efficiency and productivity of the semiconductor manufacturing plant, and generate substantial losses of potential product. The resulting off-spec microcircuitry articles thus constitute scrap which must be reworked, if this is even feasible, or else discarded as waste.

Accordingly, there is a pressing need in the semiconductor manufacturing industry to provide commercially viable systems for continuously measuring gas purity at the point of use. Such purity measurements can be used to alter process conditions that would otherwise lead to production problems, e.g., by diverting the impurity-containing gas stream to suitable treatment prior to its ultimate use in the deposition process.

In the context of general industrial processes, such as petroleum refining, wastewater treatment, biopharmaceutical production, etc., a variety of impurity monitoring and detection systems have been developed to detect fluid phase impurities, using sampling of a side stream, or slip stream, of the main flow stream for impurity concentration determination. The sampled side stream typically is flowed through the monitoring and detection apparatus and then discarded. In the field of semiconductor manufacture, such wastage is highly detrimental to the economics of the semiconductor production process when the gas stream, as is generally the case, contains costly reagent materials, e.g., organometallic source reagents for metal deposition on a substrate. Further, many gas streams employed in semiconductor manufacturing are highly hazardous in character, so that their waste presents significant difficulties in handling, treatment, and disposal.

Considering the impurities which are present in gas streams involved in semiconductor manufacturing, it is to be noted that the growth of high quality thin film electronic and opto-electronic cells by chemical vapor deposition or other vapor-based techniques is inhibited by a variety of low-level process impurities. These impurities affect both product semiconductor defects and yield.

Specifically, at least two types of contamination are significant, viz., particulate contamination and chemical contamination. Particulate contamination has been successfully addressed by a variety of filtration and collection methods and apparatus (see Malczewski, M. L., et al, "Measurement of Particulates in Filtered Process Gas Streams," Solid State Technology, 28, 151–157, April 1986). Chemical contamination has not received similar attention. As mentioned, the monitoring devices which have been developed in other industries are ill-suited for application to semiconductor manufacturing operations.

In the semiconductor manufacturing operation, chemical impurities in reactive process gases can originate in the production of the source gas itself, as well as in its subsequent packaging, shipment, storage, and handling. Although source gas manufacturers typically provide analyses of source gas materials delivered to the semiconductor manufacturing facility, the purity of such gases may change. Such change may be due to leakage into or outgassing of the containers, e.g., gas cylinders, employed to package such gases. Alternatively, impurity contamination may result from improper gas container changes, leaks into downstream processing equipment, or outgassing of such downstream equipment.

Accordingly, the only comprehensive solution for consistent delivery of high purity gases for vapor processing operations in semiconductor manufacture is the development of commercially useful impurity detection systems for real-time measurement of critical impurity concentrations in semiconductor manufacturing process streams and the deployment of reliable point-of-use purification systems for purifying gas streams which are determined to contain impurity species in excess of allowable concentrations.

The presence of even small concentrations of impurity species in the process gas streams employed in semiconductor manufacturing is potentially deleterious. Even small levels of impurities on the order of parts-per-million (ppm) can cause inconsistent electrical properties in semiconductor devices manufactured by deposition techniques using impurity-containing gas streams.

It therefore is an object of the present invention to provide a system for detection of impurity concentrations in a flowing gas stream, which can be usefully employed in semiconductor manufacturing operations.

It is another object of the present invention to provide a detection system of such type, which is capable of providing real-time monitoring of process gas streams, so that immediate correction can be undertaken when impurity concentration levels exceed predetermined set point limits.

It is a further object of the invention to provide a system for detecting impurity species in flowing gas streams, which is employed in semiconductor manufacturing operations, and which does not require any side stream or slip stream sampling for its utilization.

It is a still further object of the invention to provide a system for detecting impurity concentrations in a flowing gas stream, which is readily calibrated and has a substantial continuous service life, e.g., on the order of at least six months.

It is yet a further object of the invention to provide a system for detecting the calibrated concentration of an impurity species in a flowing gas stream, in a low concentration range, and in a high concentration range, with quick recovery to normal operation after exposure to high concentrations of impurity.

Other objects and advantages of the present invention will be more fully apparent from the ensuing disclosure and appended claims.

SUMMARY OF THE INVENTION

The present invention relates to an in-line detector system, useful for real-time determination of impurity concentrations in a flowing gas stream.

In one broad aspect, the invention relates to an in-line monitoring system for determining the calibrated concentration of an impurity species in a flowing gas stream, in a low concentration range below a predetermined concentration value, and in a high concentration range above said predetermined concentration value, said system comprising:

(a) means defining a flow path for a flowing gas stream;

(b) a gas purifier through which gas deriving from the flowing gas stream is flowable to remove impurity species therefrom;

(c) means for sensing the impurity species concentration of gas deriving from the flowing gas stream;

(d) means for selectively flowing gas from the flow path through the gas purifier to yield purified gas depleted in said impurity species;

(e) means for flowing purified gas from said gas purifier to said sensing means;

(f) means for selectively flowing gas from the flow path to the sensing means without passage of the gas through the gas purifier;

(g) means operatively coupled to said sensing means for determining a calibrated equilibrium value of impurity species concentration in the flowing gas stream from impurity species concentration in unpurified gas sensed by said sensing means in calibrative relationship to impurity species concentration of purified gas sensed by said sensing means;

(h) flow control means operatively coupled with gas flowing means (f) and (g), and arranged to selectively, alternatively and repetitively flow gas deriving from the flowing gas stream through gas flowing means (f) to the gas purifier for a first selected period of time $t_1$, and subsequently through gas flowing means (g) for a second selected period of time $t_2$, in a repeating cycle, wherein in the low concentration range below said predetermined concentration value, $t_2 > t_1$, and wherein in the high concentration range above said predetermined concentration value, $t_1 > t_2$.

In another aspect of the invention, a method is provided for determining the calibrated concentration of an impurity species in a flowing gas stream, in a low concentration range above a predetermined concentration value, and in a high concentration range above said predetermined concentration value, said method comprising:

providing an in-line monitoring system comprising:

(a) means defining a flow path for a flowing gas stream;

(b) a gas purifier through which gas deriving from the flowing gas stream is flowable to remove impurity species therefrom;

(c) means for sensing the impurity species concentration of gas deriving from the flowing gas stream;

(d) means for selectively flowing gas from the flow path through the gas purifier to yield purified gas depleted in said impurity species;

(e) means for flowing purified gas from said gas purifier to said sensing means;

(f) means for selectively flowing gas from the flow path to the sensing means without passage of the gas through the gas purifier;

(g) means operatively coupled to said sensing means for determining a calibrated equilibrium value of impurity species concentration in the flowing gas stream from impurity species concentration in unpurified gas sensed by said sensing means in calibrative relationship to impurity species concentration of purified gas sensed by said sensing means;

(h) flow control means operatively coupled with gas flowing means (f) and (g), and arranged to selectively, alternatively and repetitively flow gas deriving from the flowing gas stream through gas flowing means (f) to the gas purifier for a first selected period of time $t_1$, and subsequently through gas flowing means (g) for a second selected period of time $t_2$, in a repeating cycle, wherein in the low concentration range below said predetermined concentration value, $t_2 > t_1$, and wherein in the high concentration range above said predetermined concentration value, $t_1 > t_2$;

flowing gas from the flowing gas stream selectively from the flow path through the gas purifier to yield purified gas depleted in said impurity species, alternatingly with flowing gas from the flow path through the gas flowing means (f), and passing the gas to said sensing means; and selectively operating said flow control means (h) to flow gas through means (f) to the gas purifier for a first selected period of time $t_1$, and subsequently through gas flowing means (g) for a second period of time $t_2$, in a repeating cycle, wherein in the low concentration range below said predetermined concentration value, $t_2 > t_1$, and wherein in the high concentration range above said predetermined concentration value, $t_1 > t_2$.

In yet another aspect of the present invention, a method is provided for determining a calibrated concentration of an impurity species in a flowing gas stream, in a low concentration range below a predetermined concentration value, and in a high concentration range above said predetermined concentration value, said method comprising:

sensing the impurity species concentration of gas derived from the gas flow stream in a sequential and repetitive sensing operation wherein in a first sensing mode the gas is purified of impurity species prior to sensing thereof and wherein in a second sensing mode the gas is unpurified, and wherein in the first sensing mode and second sensing mode, the sensing mode cycle times are varied in accordance with the impurity species concentration, so that in said low concentration range below said predetermined concentration value, the second sensing mode frequency is greater than the first sensing mode frequency, and wherein in said high concentration range above said predetermined concentration value, said first sensing mode frequency is greater than the second sensing mode frequency; and determining a calibrated equilibrium value of impurity species concentration in the flowing gas stream from sensing concentrations in the first and second sensing modes.

In a still further aspect, the present invention relates to an in-line monitoring system for determining a calibrated concentration of an impurity species in a flowing gas stream, in a low concentration range below a predetermined concentration value, and in a high concentration range above said predetermined concentration value, said system comprising:

- a purifier for removing impurity species from gas derived from the flowing gas stream;
- a means for sensing the impurity species concentration of gas derived from the gas flow stream in a sequential and repetitive sensing operation wherein in a first sensing mode the gas is purified of impurity species by passage thereof through said purifier prior to sensing thereof and wherein in a second sensing mode the gas is unpurified, and wherein in the first sensing mode and second sensing mode, the sensing mode cycle times are varied in accordance with the impurity species concentration, so that in said low concentration range below said predetermined concentration value, the second sensing mode frequency is greater than the first sensing mode frequency, and wherein in said high concentration range above said predetermined concentration value, said first sensing mode frequency is greater than the second sensing mode frequency; and
- a means for determining a calibrated equilibrium value of impurity species concentration in the flowing gas stream from sensing concentrations in the first and second sensing modes.

In another aspect, the present invention relates to a method of determining a calibrated concentration of impurity species in a flowing gas stream, wherein gas derived from the gas flow stream is alternatingly sensed as to its impurity species concentration in purified and unpurified conditions, and said sensing comprises contacting of gas with a sensor including a binding medium having irreversible binding affinity for the impurity species, said method comprising sensing impurity species concentration of unpurified gas by said sensor in a differential mode, wherein sensing time of the sensor in exposure to said unpurified gas is less than 50% of the operating time of the sensor, whereby the sensor service life is extended relative to continuous sensing of unpurified gas.

In yet another aspect, the present invention relates to an in-line monitoring system for determining a calibrated concentration of impurity species in a flowing gas stream, comprising:

- a sensor including a binding medium having irreversible binding affinity for the impurity species, for sensing impurity species concentration in a gas;
- means for purifying gas derived from said flowing gas stream to yield purified gas;
- means for flowing unpurified gas derived from said flowing gas stream to said sensor and for flowing purified gas from said gas purifying means to said sensor, such that said unpurified gas is sensed by said sensor in a differential mode wherein sensing time of the sensor in exposure to said unpurified gas is less than 50% of the operating time of the sensor, whereby the sensor service life is extended relative to continuous sensing of unpurified gas; and
- means for determining a calibrated concentration of impurity species in said flowing gas stream from impurity species concentrations of said purified and unpurified gas sensed by said sensor.

In a related aspect, the present invention relates to an in-line detector system, comprising:

- a purifier unit for gas stream impurity removal; and
- means defining a flow passage assembly having an inlet end and an outlet end, and constructed and arranged:
  - for flowing at least a portion of gas from the flowing gas stream through the purifier unit to yield impurity-reduced gas;
  - for flowing impurity-reduced gas to an impurity concentration sensing locus;
  - for flowing unpurified gas from the flowing gas stream to an impurity concentration sensing locus; and
  - for discharging the impurity-reduced gas and unpurified gas from the outlet end.

Another related aspect of the invention relates to an in-line detector system whose sensitivity may be conveniently recalibrated periodically, comprising:

- a purifier unit for gas stream impurity removal; and
- means defining a flow passage assembly having an inlet end and an outlet end, and constructed and arranged:
  - for flowing at least a portion of gas from the flowing gas stream through a purifier unit to yield impurity-reduced gas;
  - for flowing at least a portion of impurity-reduced gas to an impurity concentration sensing locus;
  - for flowing at least a portion of the gas stream to an impurity standard locus which transmits a known impurity concentration to the gas;
  - for flowing gas from the impurity standard locus to the impurity concentration sensing locus.

In another related aspect, the present invention relates to an in-line detector system, comprising:

- a purifier unit for removing impurity from gas containing same;
- a manifold assembly having an inlet joinable in flow communication to the flowing gas stream for passage of the flowing gas stream therethrough, and an outlet for discharging from the manifold assembly gas flowed therethrough, with such manifold assembly defining (i) a first flow path coupled to the purifier unit for passing gas from the flowing gas stream through the purifier unit to yield impurity-reduced gas, and (ii) a second flow path bypassing the purifier, constructed and arranged such that the manifold assembly derives from the flowing gas stream first flow path and second flow path gas streams, and discharges same through the outlet of the manifold assembly;
- means for (a) sensing gas impurity concentration of impurity-reduced gas discharged from the purifier unit into the first flow path of the manifold assembly, as a baseline impurity concentration value, (b) sensing gas impurity concentration in the second flow path gas stream, and (c) determining therefrom a baseline-adjusted impurity concentration value for the flowing gas stream.

In a further related aspect, the present invention relates to an in-line detector system whose sensitivity can be conveniently calibrated periodically, additionally comprising:

(i) a first flow path coupled to a purifier unit for passing gas from a flowing gas stream through the purifier unit to yield impurity-reduced gas, and subsequently passing the impurity-reduced gas through an impurity standard locus where a known concentration of impurity is imparted; (ii) a second flow path bypassing the impurity standard locus, constructed and arranged such that the manifold assembly derives from the flowing gas stream first flow path and second flow path gas streams, and discharges same through the outlet of the manifold assembly;

means for (a) sensing gas impurity concentration of gas discharged from the impurity standard locus into the first flow path of the manifold assembly, as a baseline impurity concentration value, (b) sensing gas impurity concentration in the second flow path impurity-reduced gas stream, and (c) determining therefrom a standard impurity concentration value which is used to calibrate the detector.

The purifier unit in the broad practice of the invention may be of any suitable type, but preferably comprises a vessel containing a bed of a scavenger material which is sorptively selective for the impurity in the flowing gas stream.

The manifold assembly may be variously configured, and in one aspect may comprise a main gas flow conduit to which is joined, in spaced-apart relationship to one another, the purifier unit and a sensor port coupleable with suitable impurity concentration sensing means. In this assembly, a T-shaped conduit member is utilized having a vertically depending leg joined at a lower end thereof to the main gas flow conduit, and at an upper end thereof to laterally extending arms. The outer ends of the laterally extending arms are respectively joined to the purifier and the sensor port, with a switcher valve, e.g., a pneumatic valve or an electrically controlled solenoid, disposed at the intersection of the arms and leg of the T-shaped conduit member, to selectively establish flow from the main gas flow conduit through the purifier unit to the sensor port, or alternatively through the leg and an arm of the T-shaped conduit member to the sensor port.

Alternatively, the manifold assembly may be configured with an inlet gas flow conduit joined to an inlet gas manifold which at its extremities is joined to respective first and second branch flow conduits, and with the branch flow conduits joined at their opposite ends to an outlet gas manifold which in turn communicates with an outlet gas flow conduit attached to the outlet gas manifold. With such manifold assembly, a purifier unit may be disposed in one of the manifolds or branch flow conduits upstream of a first impurity sensor, while a second impurity sensor is disposed either upstream of the purifier unit, or else in an opposite portion of the manifold assembly through which gas is not flowed to the purifier unit. In this manner the respective impurity sensors constitute a reference sensor (downstream from the purifier unit) and a sample sensor (the sensor deployed in the portion of the manifold assembly through which the gas stream is not flowed to the purifier unit), and the sensing of the reference and sample sensors may be employed to determine a baseline-adjusted concentration value for the impurity in the gas stream.

In a preferred aspect, the impurity concentration sensing means, when water is the impurity species, comprises a hygrometric or alternatively a piezoelectric-based concentration sensor. For non-aqueous impurity species, a piezoelectric-based device preferably is employed, such as a surface acoustical wave (SAW) device.

Another aspect of the invention relates to SAW devices comprising specific affinity coatings on the piezoelectric substrate of the device, as specific to particular impurity gas species.

Other aspects of the invention relate to in-line detector systems of the type broadly described above, as associated with sensors and signal generating and processing means for determining a baseline-adjusted concentration value of the impurity in the flowing gas stream.

Other aspects of the invention include appertaining methodology for determining impurity concentration in a flowing gas stream by in-line detection, wherein gas from the flowing gas stream is purified and sensed to determine its impurity concentration, together with sensing of the impurity concentration of gas from the flowing gas stream which has not been purified, and a calibrated, or baseline-adjusted, concentration value is determined for the impurity in the flowing gas stream.

Other aspects and features of the invention will be more fully apparent from the ensuing disclosure and appended claims.

DETAILED DESCRIPTION OF THE INVENTION AND

PREFERRED EMBODIMENTS THEREOF

Figure 1:
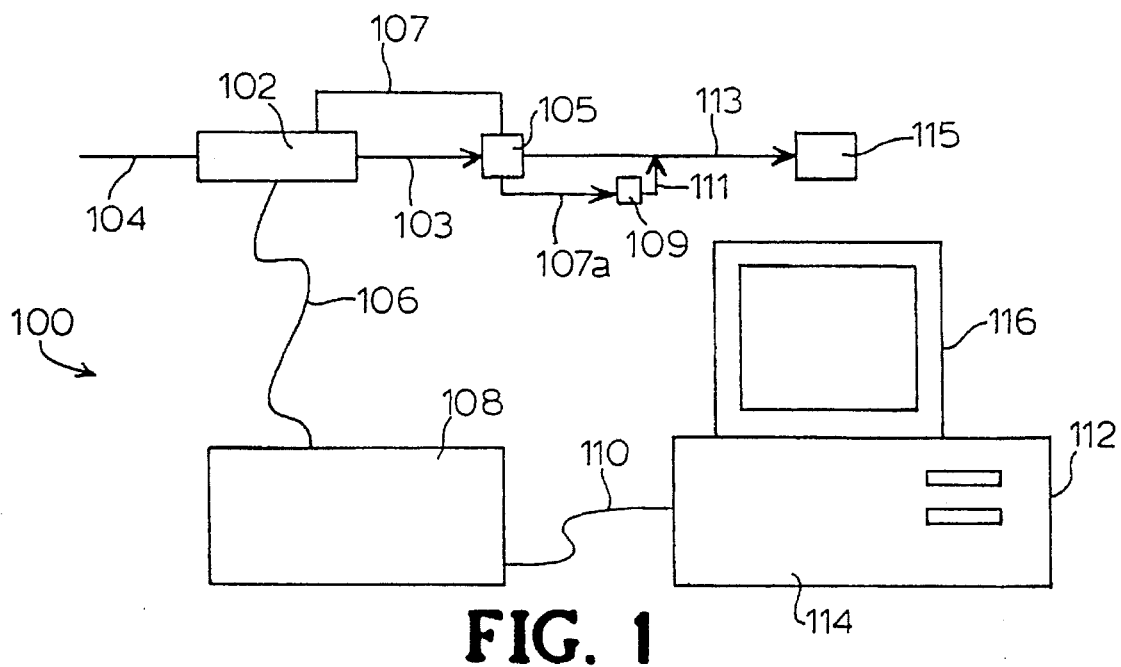
FIG. 1 is a schematic representation of a detector system according to one embodiment of the present invention.

The present invention overcomes the deficiencies of prior art gas monitoring systems, as described in the "Background of the Invention" section hereof, by the provision of an in-line gas impurity detector and monitoring system which is specifically adaptable for use in the manufacture of semiconductor devices including vapor deposition-based processes.

The detector system of the present invention enables the concentration of critical impurities in a flowing gas stream to be measured at low levels (e.g., part-per-billion concentrations), thereby permitting impurity concentrations in the flowing gas stream to be controllably maintained at suitably low levels for efficient semiconductor device manufacturing, and may be usefully employed in combination with means for initiating purification treatment of the flowing gas stream when impurities therein exceed acceptable set point limits. The detector system of the present invention can monitor concentration of an impurity species in a flowing gas stream, in a low concentration range, and in a high concentration range, with quick recovery to normal operation after exposure to high concentrations of impurity.

Since the detection system of the present invention is an in-line system, there is no wastage of the process gas, or hazards occasioned by its diversion, treatment, and disposal, such as is the case in impurity concentration monitoring systems in which side streams are separated from the main gas flow stream and passed to remote concentration sensing means.

Because the detection system of the present invention is capable of being calibrated both as to the sensor's baseline (or "zero point") and at a known impurity concentration preferably typical of the impurity concentrations that might be found in the flowing process gas stream, the detection system can use impurity sensors that are readily available and economically feasible, despite the fact that these sensors may undergo some drift with time in both baseline and response curve.

As a result, the in-line detector systems of the present invention permit consistent delivery of high purity gases to be achieved, with direct, real-time measurement of critical impurity concentrations in process gas streams. In conjunction with the use of such detection systems, the deployment of in-line, point-of-use purification systems enables gas purification to be correctively undertaken so that predetermined purity set point limits for the flowing gas stream are readily and continuously maintained.

Examples of gas purification systems which may be usefully employed in conjunction with the in-line detector systems of the present invention, include the purifier apparatus, compositions (scavengers or chemisorbents), and methods disclosed and claimed in U.S. Pat. Nos.: 4,761,395 (composition for purification of arsine, phosphine, ammonia, and inert gases); U.S. Pat. No. 4,853,148 (hydrogen halide purification); U.S. Pat. No. 4,797,227 (hydrogen selenide purification); U.S. Pat. No. 4,781,900 (method of purifying arsine, phosphine, ammonia, and inert gases); U.S. Pat. No. 4,950,419 (composition for inert gas purification); U.S. Pat. No. 5,015,411 (inert gas purification method); U.S. Pat. No. 4,865,822 (hydrogen selenide purification method); and U.S. Pat. No. 4,925,646 (hydrogen halide purification method); U.S. Pat. No. 5,057,242 (composition for purifying chlorosilanes); U.S. Pat. No. 5,094,830 (chlorosilanes purification method); applicant's co-pending U.S. Pat. application Ser. No. 08/084,414 (purification of inert and hydride gases); as well as the purifier vessel apparatus disclosed and claimed in U.S. Pat. Nos. 4,723,967 and 4,738,693, all of which hereby are incorporated herein by reference.

The in-line detector systems of the present invention may be utilized with any suitable specific gas impurity concentration sensors, which provide output indicative of impurity concentration in the gas stream. Such sensors may be hygrometric (in the case of monitored aqueous contaminants such as water), spectrophotometric (based on transmissivity or reflectivity of radiation impinged on the gas stream), piezoelectric, colorimetric, etc., in character or may otherwise incorporate any suitable means, method, or modality of operation, as desired, for quantitation of the selected impurity species in the flowing gas stream being monitored. The active medium of the sensor typically is a medium having a binding affinity for the species of interest, such as a physical adsorbent material.

Generally, in semiconductor manufacturing operations, the most critical impurity species is water vapor, and the presence of water in the gas stream often is indicative of atmospheric contamination of the process system. Accordingly, the invention will be illustratively described hereinafter primarily with reference to detection of water as the impurity species of interest. It will be recognized however, that such focus is for descriptive purposes only and that the invention is broadly practicable in monitoring of any other impurity species, for which suitably sensitive sensors exist. Illustrative examples of impurity species and corresponding potentially useful sensor media include, but are not limited to: water/alumina (hygrometer), HCl/alumina (hygrometer), water/polyamine (piezoelectric detector), water/$P_2O_5$ (electrolytic detector; has an irreversible component), ammonia/alumina (hygrometer), methanol/alumina (hygrometer), oxygen/tin oxide (solid state electrode).

While the specific structure and function of the in-line detector systems may be widely varied within the broad scope of the present invention, such in-line detection systems must meet various functional criteria, as set out below.

First, the detector system must be non-contaminating in character, with respect to the gas stream being processed. Since the flowing gas stream after its monitoring (and verification of suitably low impurity concentration therein) is flowed to the deposition reactor or other locus of use, any contaminants deriving from the detector system will subsequently be distributed throughout the process system. This may have a significant and deleterious effect on the products being manufactured. Accordingly, any impurities introduced from the in-line detector system itself should be suitably low, e.g., in the part-per-billion (ppb) range or lower.

Thus, the detector system must be mechanically tight and leak-free in character. This requirement dictates the use of correspondingly suitable materials of construction in the detector system, with the parts and components of the detector system having a high finish on those parts and components which are in contact with the gas stream, and with all seals of the detector being of a face seal, leak-tight character.

A preferred material of construction is stainless steel of suitably high finish quality. If any particulates are generated in the use and operation of the detector, particle filters may be required components of the system.

In addition, the detector system should accurately measure the critical impurities in the process stream. Process gas streams employed in the semiconductor manufacturing industry typically contain more than one impurity, and it would be highly advantageous to accurately measure the concentration of each of such impurities in the gas stream.

As a practical consideration, however, there does not exist a single sensor which is able to measure all possible impurities. Monitoring all impurities of interest would therefore require a large multiplicity of sensor devices, which would in turn unduly complicate the design and operation of the detector system.

Accordingly, in multicomponent impurity-containing gas streams, it is preferable to select a single impurity species and monitor same, particularly where the impurity species monitored is a limiting or most critical impurity, or where the specific impurity species is quantitatively correlative with other impurity species present in the multicomponent impurity-containing gas stream.

As indicated hereinabove, a critical impurity in semiconductor manufacturing operations is water, and a variety of water sensors is readily available. By contrast, oxygen, while also an important impurity species, is frequently a poor choice for process gas monitoring purposes, since oxygen sensors are poisoned by many of the (semiconductor manufacturing) gas streams of interest, so that as a practical matter, viable sensors are not available. In this respect, it should be borne in mind that the sensors required are preferably sub-part-per-million (ppm) level sensors.

It will be recognized that in the instance where the impurity species is a potential poison to the sensor element, the differential sensing mode of the present invention may afford a manner of extending the sensor life to periods of time which in the absence of such operation would be practically unobtainable.

Thus, the detector system should have the requisite sensitivity for detection of gas impurities, preferably on the level of parts-per-million and most preferably on the level of parts-per-billion.

Further, the detector system should desirably be stable for substantial periods of time, e.g., at least six months, and preferably on the order of one year or more, without recalibration continually being required. Thus, the sensors used in the detector should be of a non-drifting character, or if drift is necessarily present, means should be provided to self-correct the concentration measurement so that stable and consistent quantitative operation is achieved, with respect to the impurity concentration in the gas stream being monitored. Such means of self-correction should include calibration of both baseline and sensitivity to known impurity concentration, since both baseline and response curve may drift with time.

Additionally, the cost of the detector system should be suitably low to ensure ready commercial deployment, with economic, readily available sensor devices being utilizable in the detector system.

The foregoing criteria are accommodated in the broad practice of the present invention by the provision of a detector system in which gas from the flowing gas stream (either a portion of such stream, or the entire stream itself) is passed through a purifier in which the impurity being monitored is substantially completely removed from the gas. The impurity concentration of the resulting purified gas is then sensed to provide a baseline concentration sensing value. Contemporaneously, gas from the flowing gas stream, which is not purified by the aforementioned purifier unit, is subjected to impurity concentration sensing means. This provides a sensed concentration value which is employed, together with the impurity concentration sensing valve for the purified gas, to provide a calibrated value of impurity concentration for the flowing gas stream.

The gas passed through the purifier and subsequently sensed for impurity concentration, is discharged from the detector system in the flowing gas stream, and the sensed gas which has not been purified likewise is discharged from the detector system in the flowing gas stream. By this arrangement, none of the influent flowing gas stream passed through the detector system is diverted to waste, or otherwise requires final disposition as a result of its being monitored for impurity content (the only exception is the impurity species which is removed from gas in the purifier, e.g., which is typically present in the gas flowed to the purifier at a low concentration, e.g., less than about 1,000 ppm and more typically less than 100 ppm).

Correspondingly, the sensor which is employed with the in-line detector system should have a suitably low detection limit, preferably sub-ppm levels, and more preferably down to 100 parts-per-billion (ppb), or lower.

Among the various types of sensor devices described hereinabove (hygrometric, spectrophotometric, etc.), a preferred sensor is of piezoelectric-type, in which the characteristics of the piezoelectric surface thereof are altered by the presence and any change in concentration of the impurity species being monitored in the detector system.

A particularly preferred piezoelectric device comprises a surface acoustical wave (SAW) device. SAW devices are piezoelectric electronic components which traditionally have been used as narrow band frequency filters, e.g., frequency-determining elements in high frequency control applications. Such devices operate by passing a signal across a piezoelectric thin planar substrate as an acoustic wave. The acoustic wave is created by imposing an AC electrical signal on a metallized interdigital electrode which is plated on the surface of the substrate at one end. This acoustic wave is transmitted across the substrate to a symmetrically formed metallized interdigital electrode (transducer) at the opposite end. The receiving transducer converts the acoustic signal back to an electric signal. The electrical characteristics of SAW devices can be tailored to specific application by varying the finger spacing of the interdigital transducers, the space between transducers, and the thickness of the substrate, as is well known to those skilled in the art, to control the frequency, propagation delay, and acoustic wave mode of the signal transmitted across the device.

For monitoring low moisture levels, a preferred sensor type is hygrometric, wherein a property such as capacitance of a material which has a high sorptive affinity for water is monitored. Such hygrometric sensors have as the active sensing material substances such as ultra-dry alumina, which adsorb water with high affinity. Other contaminant species which may be sensed by such hygrometric sensors include polar compounds such as ammonia, methanol, etc.

Regardless of the specific type of impurity concentration sensor employed in the broad practice of the present invention, the sensor should possess the sensitivity to measure the concentration of the critical impurities at sufficiently low levels consistent with the high purity character of the gas streams being monitored by the detection system.

In most semiconductor processing applications of the in-line monitor, the sensing means preferably has extremely high sensitivity, because the amount of moisture or other contaminant species present in the gas stream is typically quite low under normal operating conditions, e.g., a few parts per billion. Examples of highly responsive sensors include capacitive hygrometers, which measure trace levels of moisture by monitoring the capacitance of a material such as ultra-dry alumina, which has an extremely high affinity for water. The alumina or other active sensor material, in contact with the gas stream, binds trace levels of contaminant it encounters, manifesting as a change in capacitance of the sensor material. Piezoelectric detectors bind the contaminant to a high affinity layer on the surface of the detector, manifesting as a change in the frequency of the vibrations of the film because of the change in its weight.

Many of the most highly sensitive detectors operate by interacting with the analyte via sorption, physical association, aggregation, or other binding process, and do so with high affinity. When such a sensor material, interacting with the analyte by a physical sorption process, encounters high concentrations of analyte, e.g., moisture or other monitored contaminant, as it may do in the event of a serious leak or compromise of the gas handling system, it may not be able to reequilibrate to the lower level of contaminant sufficiently quickly for convenient operation. A long "dry-down" period may be required, during which the usefulness of the in-line-monitoring system is seriously compromised. This limitation can be a major problem if high contaminant levels are encountered in a gas stream during an "upset," e.g., a major leakage event, compromise of the gas handling system, inadvertent flowing of the wrong gas or vapor phase reactant into the process, or other abnormal situation in which the sensor material encounters a large bolus of the analyte (contaminant being monitored for).

In impurity-sensitive vapor-phase operations, e.g. semiconductor device processing or vapor phase coating of fiber-optic filaments, protection of the process from exposure to the high contaminant concentrations that could be encountered in these "upset" events is crucial and is an important function of the in-line monitoring system. During an upset, the concentrations of moisture or other contaminants can be very high. Semiconductor processors have indicated that they want to be able to estimate moisture levels to 20 part per million (ppm), which is significantly higher than the few parts per billion (ppb) levels encountered in a process that is running smoothly. If the highly sensitive, sorption-based sensors described above reach equilibrium at the higher contaminant level, they may take hours to days of "dry-down" for the output signal to recover to the baseline level.

The solution to the problem of slow recovery/response time is to operate the in-line monitor in a differential mode, in situations where high concentrations of contaminant are encountered. In the normal mode, the sensor is exposed the majority of the time to the sample gas (the gas stream whose impurity level is being monitored). The characteristics of the sensor in this normal mode are high sensitivity and an output signal that reflects the full equilibration of the sensor with the gas stream. In the differential mode, the sensor is left in the purifier mode, that is, it is exposed the majority of the time to the gas stream that has passed through the purifier module. For a short period of time, the by-pass valve is opened. The sensor takes a short look at the sample gas stream. The by-pass valve is then closed and the system is allowed to recover. The cycle then repeats. Using the output signals from the brief exposures to the high contaminant sample gas stream, the system then extrapolates the change in contaminant concentration to the equilibrium value.

A sensor material which interacts with the analyte by physical sorption, e.g., a hygrometer or SAW device, behaves like a sponge. If the sponge is left in a spray of water for a long time, switching to a drying gas will require a long period of time to dry out the sponge. If the sponge is sprayed very briefly and returned to the dry gas stream, recovery is fast.

The key to operation in the differential mode is to allow surface equilibration but not bulk equilibration of the sensing medium. Measurements are made at dynamic contact equilibrium rather than at static equilibrium of the sensing medium, where the dynamic contact equilibrium is a surface equilibrium phenomenon, and the static equilibrium is a bulk equilibration condition. The in-line monitor is configured so that it is possible to selectively, alternatively and repetitively flow gas deriving from the gas stream being monitored through the gas purifier module for a first selected period of time $t_1$, and subsequently through the contaminant sensing module for a second selected period of time $t_2$, in a repeating cycle. The time $t_1$ is chosen such that exposure of the sensor to the purified gas is adequate to permit accurate baseline concentration calibration, with some baseline drift being allowable in practice, since impurity concentrations are measured by difference. Time $t_2$ is chosen to allow dynamic contact equilibrium to occur but not static equilibrium, and the detector can therefore recover much more quickly to equilibrium with the low-contaminant concentration gas stream, without changes in its response curve. The actual concentration of contaminant in the gas stream being monitored is derived by extrapolating the change in contaminant concentration to the equilibrium value.

The cycle times will depend on the nature of the contaminant species and the sensor, the sorptive affinity of the sensing or binding medium for the contaminant species, the gas flow rate, the contact time with the sensing medium, and other system parameters. For a sensor comprising a binding medium with high sorptive affinity for the contaminant species, the binding medium would typically be exposed to the sample gas for a time period many-fold less than the exposure time to the purified gas stream (or "zero gas"), on the order of 5–100 fold less. For example, the binding medium could be exposed to the sample gas for time for a few seconds to minutes, e.g., 10–60 seconds, followed by exposure to the zero gas for a time period on the order of a few to tens of minutes, e.g. 3–30 minutes.

Referring now to the drawings, FIG. 1 shows a schematic diagram of an in-line detection system 100, comprising an in-line detector assembly 102. Conduit 104 is joined to the detector assembly and conveys the high purity gas stream to the assembly for monitoring therein of the concentration of critical impurity species. Monitored gas is discharged from the detector assembly in line 103 and is passed to flow controller 105, which is coupled to the detector assembly in signal transmitting relationship by means of flow control signal line 107. If the monitoring of the critical impurity species reveals that the concentration is above set point limits, the flowing gas stream is diverted by the flow controller 105 into bypass line 107a and flows into gas scrubbing or purification complex 109 in which the impurity species is removed to below the maximum set point concentration value. The resulting scrubbed gas then is passed in line 111 to the process gas delivery conduit 113 and is discharged into the vapor-phase processing complex 115.

If the concentration of the critical impurity species monitored by detector assembly 102 is within allowable set point limits, the flowing gas stream in line 103 is passed by the controller 105 to delivery line 113 for passage to the downstream, end use complex 115. Complex 115 may, for example, comprise a chemical vapor deposition reactor or other suitable downstream processing equipment.

Joined to the in-line detector assembly 102 in signal transmitting and receiving relationship, via signal line 106, is a controller 108. This controller may include optoelectronic converters, digital/analog circuitry, etc., by means of which the sensing of impurity species by the in-line detector assembly 102 is convertible to a processing signal. This processing signal is transmitted by signal transmitting means 110 to a digital computer 112 comprising central processing unit 114 and monitor or display 116. Alternatively, the digital computer 112 may be replaced by microprocessor, programmable logic device, or other calculational means which are incorporated in or otherwise integrated with the controller 108.

In operation of the FIG. 1 system, the in-line detector assembly 102, coupled with a suitable sensor or sensors, is arranged to sense concentration of critical impurity species in the flowing gas stream, as well as to sense the critical impurity species concentration of gas from the flowing gas stream which has been subjected to purification.

These respective concentration sensings then are passed by signal transmitting means 106 to controller 108, and converted to the requisite form (of a processing signal) for computational purposes. The processing signal is passed by processing signal transmitting means 110 to digital computer 112 for determination of an on-line, real-time concentration value, as corrected (normalized) by the purified gas (impurity concentration sensing) valve.

The normalization (correction) of sensing of critical impurity species in the flowing gas stream, by correspondingly sensing the critical impurity species in a purified stream of the gas from the bulk flowing gas stream passed to the in-line detector, is a critical aspect of the present invention, which eliminates problems that may occur in sustained operation of the detector system as a result of sensor "drift".

Thus, with the high sensitivities desired of the sensors in the broad practice of the present invention, e.g., below 1000 parts-per-million, preferably below 100 parts-per-million, more preferably below 10 parts-per-million, and most preferably below one part-per-million, the sensors invariably have a tendency to drift (change in accuracy) with time. This is particularly true in continuous operation or near-continuous operation semiconductor manufacturing plants, in which gas is flowed through the detector system over sustained periods of time. Both the baseline signal and the response curve may drift over time. Such alteration of sensitivity and accuracy of the sensors with time, unless continuously corrected, can insidiously lead to gas impurity concentrations exceeding proper set point limits without being identified as "out of spec". This in turn may cause excessive amounts of impurities to be present in layers and films deposited on substrates in the subsequent vapor-phase processing operations. The resulting inclusions of gross amounts of impurity species in product devices which can render them deficient or even useless for their intended purpose.

The baseline drift problems associated with high sensitivity sensor(s) in the detection system are self-corrected in the practice of the present invention, by sensing the concentration of impurity species in gas derived from the bulk flow stream, after it has been purified in an in-line fashion, with such purified gas impurity sensing then being employed as a baseline corrective value or condition for the sensing of impurities in the (unpurified) bulk flow stream.

In conjunction with self-correction of the sensor baseline, any drift in the response curve of the sensor in the detection system can also be self-corrected in the practice of the present invention, by the provision of one or more known concentrations of impurity species to the sensor, by means of which the sensor's response curve may be re-calculated. Recalibration of both baseline and response curve may be performed periodically without taking the sensor off-line.

By "in-line detection" as used herein is meant that the flowing gas stream of interest is sensed as to its impurity concentration, and also is at least in part purified to provide a baseline impurity concentration sensing, with both sensings being carried out in the same general locus, and with any gas in circulation loops employed for sensing purposes being redirected into the bulk gas flow stream for ultimate delivery to the downstream processing facility, e.g., chemical vapor deposition reactor.

Figure 2:
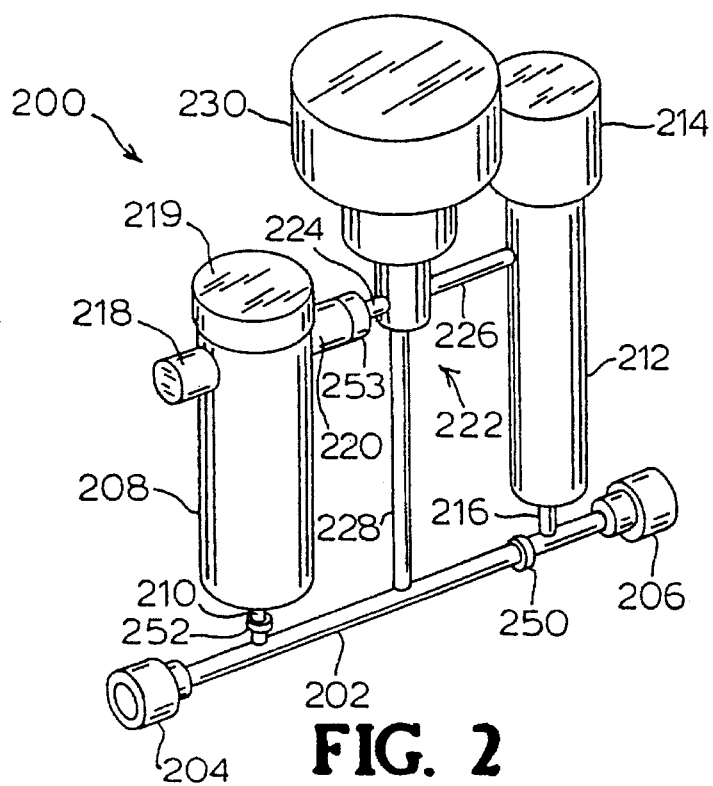
FIG. 2 is a perspective view of a detector system assembly according to one aspect of the present invention, such as may be usefully employed in the practice of the invention to sense impurity concentrations in flowing gas streams.

Referring now to FIG. 2, there is shown a perspective view of an in-line detector assembly 200, comprising an inlet gas flow conduit 202 with an inlet fitting 204 at one end, and connected in flow relationship to a outlet gas flow conduit 205 with an outlet fitting 206. A purifier vessel 208 is joined in inflow relationship to the main conduit 202 by means of purifier feed conduit 210.

The in-line detector assembly 200, by means of the respective inlet and discharge fittings 204 and 206, may be coupled in an "in-line" fashion to a gas stream which ultimately is passed to a chemical vapor deposition (CVD) reactor, or other vapor-phase processing apparatus.

As appearing subsequently herein, identifications of a component of the detector system being joined "in inflow relationship" to another component of the system, means that the components are constructed and arranged so that the gas stream flows from the first-mentioned component to the second-mentioned component. Correspondingly, the identification of a detector system component as being joined "in outflow relationship" to another system component, means that the respective components are constructed and arranged so that the gas stream from the first-mentioned component is discharged (through any suitable flow communication means) to the second-mentioned component of the system.

Downstream of the purifier feed conduit 210, and in proximity to the discharge fitting 206, is provided an impurity sensor port 212, with an upper fitting 214. By means of the upper fitting 214, the sensor port may be coupled to a suitable sensor, such as a hygrometric sensor for water vapor detection, or a SAW device for detection of water, nitrogen oxides, hydrogen sulfide, or other critical impurity of interest. The sensor port 212 is joined to the outlet fitting 206 by means of gas flow conduit 216.

The purifier unit 208, depending on the impurity species, may comprise a fluid-tight vessel filled with a bed of a suitable scavenger material. The scavenger material may for example comprise a scavenger of a type as disclosed in U.S. Pat. Nos. 4,761,395; 4,853,148; 4,797,227, in a purifier vessel 219 of the type disclosed and claimed in U.S. Pat. No. 4,723,967 or U.S. Pat. No. 4,738,693. The purifier vessel 208 may suitably be provided, if desired, with a pressure transducer port 218, for measurement of pressure in the purifier unit. The purifier vessel 208 also features an outlet port 220, by means of which purified gas is discharged from the purifier unit.

The detector assembly shown in FIG. 2 further comprises a manifold 222 interconnecting the purifier unit 208 with the sensor port 212, by means of lateral conduits 224 and 226. Lateral conduit 226 also is joined to the inlet flow conduit 202 by means of manifold 222. Disposed in the manifold 222, at the locus of intersection of the conduits 224, 226, and 202, is a switcher valve 230. This valve preferably is an automatic control-type valve which is selectively switchable between (1) a first position for effecting flow of gas through the manifold, in conduits 224 and 226 thereof, from the purifier unit 208 to the sensor port 212, and (2) a second position for effecting flow of gas to the manifold from the main flow conduit 202, and through lateral conduit 226 to the sensor port 212.

Disposed within the purifier 208 (and not shown) are two flow restrictors, whose role is to retain the purifier's scavenger bed and regulate the pressure drop of the gas flow pathway through the purifier. These flow restrictors may be of any suitable type which are adaptable to provide the flow restriction and pressure drop characteristics necessary in the detector system. The flow restriction characteristics of these flow restrictions may include different pressure drops, as in the illustrative detector system herein described. Alternatively, in some instances it may be desirable for the flow restriction characteristics of the flow restrictors to be the same. The flow restrictors preferably comprise disk-shaped elements, or "frits," constructed of sintered metal, porous ceramic, or other flow-permeable medium which is compatible with the gas stream constituents, and is efficacious for its intended purpose in terms of pressure drop and flow restriction character.

Preferred restrictor elements include stainless steel frits which are commercially available from Mott Corporation (Farmington, Conn.). Such elements are available in the form of 5–100 micron average pore size disks.

In operation of the system shown in FIG. 2, the inlet fitting 204 of the main gas flow conduit 202 may be coupled to piping or tubing through which the bulk gas stream is flowed to the detector system, and the discharge fitting 206 of such conduit is likewise coupled to suitable piping or tubing for the delivery of the bulk gas flow stream to the downstream processing apparatus. The back-pressure created by the purifier scavenger resin bed and the flow restrictors that retain scavenger resin bed in place causes some of the gas to flow through the purifier feed conduit 210 and some to continue to flow through conduit 202 of manifold 222, depending on the setting of the switcher valve 230. The switcher valve suitably is coupled to automatic controller means (not shown), such as a microprocessor-controlled timer actuator for the valve. The switcher valve may be of any suitable type; preferred types include pneumatic valves and electrically controlled solenoids.

The flow restrictors within the purifier provide containment of the scavenger or other sorbent material which is provided in the form of a bed in purifier unit 208. As a result of gas flow through the bed of scavenger or sorbent material in the purifier unit, particulates may otherwise be susceptible of migrating into feed conduit 210 or manifold conduit 224, if the restrictors were not present. In addition, the flow restrictors provide back pressure for the purifier loop defined by feed conduit 210, purifier unit 208, discharge port 220 and conduits 224 and 226 of manifold 222.

When the switcher valve 230 is selectively positioned in a first position, gas from the main gas flow stream in conduit 202 flows through purifier unit feed conduit 210 into purifier unit 208 where the impurity species is removed from the gas to produce an impurity-reduced gas stream. This purified gas stream is discharged from the purifier unit in discharge port 220, and passes through conduits 224 and 226 to the sensor port 212 for sensing by a sensor (not shown) which is operatively joined to the sensor port by means of coupling 214.

If the switcher valve 230 is switched to a second position, the gas flowing in conduit 202 will bypass the purifier loop and gas will flow through conduits 202 and 226 of the manifold 222, and enter the sensor port 212, so that sensing of the impurity concentration in the gas stream can be effected. Regardless of whether the gas entering the sensor port 212 passes through the purifier loop, or passes through manifold conduits 202 and 226, the gas is discharged therefrom in outlet conduit 205 for discharge through the outlet fitting 206 into the connecting piping or tubing (not shown) and delivery to the downstream processing apparatus.

By this arrangement, all of the gas flows in the detector assembly can be manipulated by a single valve. The sensor port 212 may be coupled with a suitable sensor, e.g., an alumina hygrometer sensor, by means of sensor coupling 214.

By means of the detector assembly in FIG. 2, the monitoring of gas impurity concentration is carried out with no waste stream. All flows from the main flow conduit passing to the sensor port are returned to the main gas flow stream with no loss. Further, the detector assembly comprises a purifier unit which provides a non-drifting zero measurement point. As a result, it is possible to continuously correct the sensor in the course of operation of the detector assembly, yielding a stable sensing system for extended periods of time. In addition, since the impurity-containing gas from the main gas flow stream, as well as the impurity-reduced gas yielded by the purifier unit, are passed sequentially to a common sensor port, the utilization of a single sensor is facilitated, which obviates the problems associated with differing drifts of accuracy and sensitivity when multiple sensors are employed.

While the present invention preferably is practiced by using a single sensor in connection with the in-line detection assembly of the invention, as for example is accommodated by the detector assembly shown in FIG. 2, the invention may also be carried out with multiple sensors, as will be described more fully hereinafter. It is to be recognized that the use of multiple sensors, due to the aforementioned drift phenomena, may require periodic recalibration in order to maintain accurate and reliable monitoring of gas impurities in gas streams flowed through the detector assembly.

Figure 3:
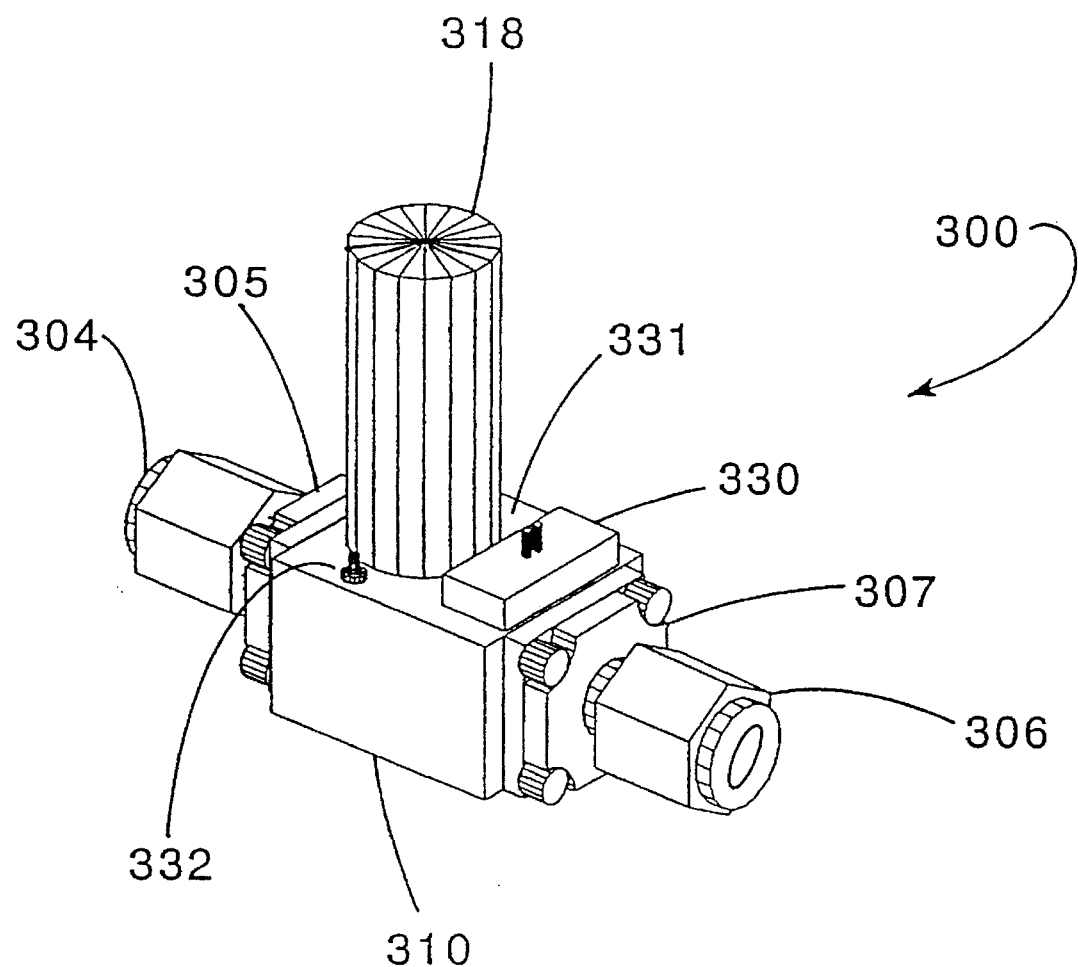
FIG. 3 is a perspective view of the detector system assembly of FIG. 2, schematically shown as being mounted in a modular housing.

Referring now to FIG. 3, a detector assembly 300 of the type shown in FIG. 2 is shown as being constructed in a unitary housing 310, which may be of block-like form as shown. Inlet port 304 and outlet port 306 are bolted to the main housing 310 by flanges 305 and 307 respectively. Purifier 318 extends exteriorly of the housing 300. Boss 330 holds the sensor in place within housing 310, and from boss 330 extend electrical leads 331 which carry the signal from the sensor to a signal displaying means or to a controller unit which responds to the signal. Port 332 is an air supply inlet to provide compressed air to operate an air-actuated valve (not shown; corresponds to valve 230 in FIG. 2) within housing 300. By this arrangement, the overall detector assembly 300 represents a unitary, easily mounted structure, which is readily deployed, in-line, in a bulk gas flow stream for detection of impurity concentrations therein.

The fittings 304 and 306 may be any of a number of suitable types including VCR, VCO or Swagelok, depending upon the requirements of the application the gas flow is being employed in. Because flanges 305 and 307 are used as means for connecting the fittings to the housing 310, great flexibility in selection of off-the-shelf fittings is possible while conserving all the key features of the in-line detector assembly.

Figure 4:
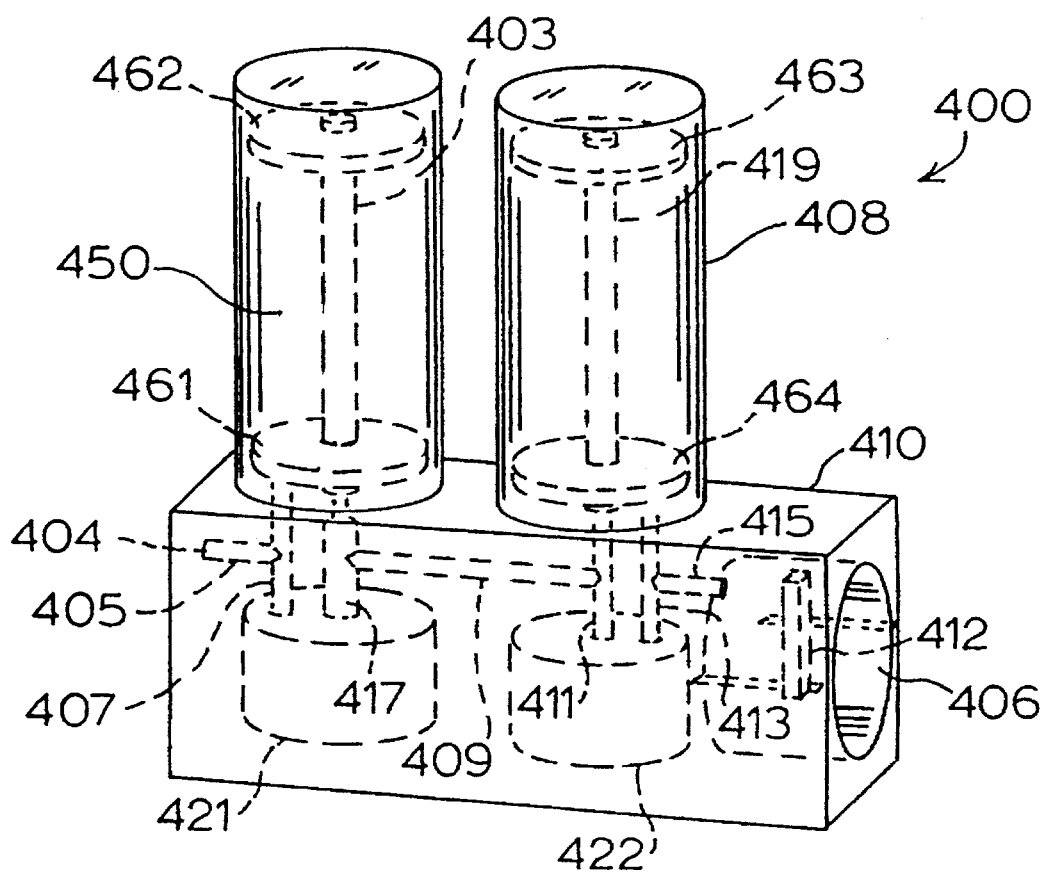
FIG. 4 is a perspective view of a detector that may be periodically recalibrated at two concentrations, a baseline concentration and a well-characterized, non-zero value of impurity concentration in a flowing gas stream, having a means for calibration at the low, baseline impurity concentration and at the higher well-characterized impurity concentration.

FIG. 4 is a perspective view of a detector system 400 according to another embodiment of the present invention. This embodiment provides calibration of the sensor baseline and calibration of the detector sensitivity at a known concentration of impurity species, provided the gas stream flow rate is known and constant.

As illustrated, the detector assembly 400 comprises a housing 410 within which are mounted valves, gas flow conduits and sensor and above which extend an impurity source 450 and a purifier 408. In the normal sensing mode of operation, valves 421 and 422 are in the open position. The gas flow stream enters the detector assembly at entry port 404 and flows through the detector assembly as follows:

through gas flow conduit 405, vertical gas flow conduit 407, open valve 421, gas flow conduit 417, gas flow conduit 409, gas flow conduit 411, open valve 422, gas flow conduit 413, gas flow conduit 415, passing into the space around sensor 412 and contacting the sensor, outlet port 406. Sensor 412 produces a signal in response to impurity and is coupled to a means for displaying the signal or to a controller unit which processes the signal.

In the baseline calibration mode, valve 421 is in the open position and valve 422 is closed. The gas flow stream enters the detector assembly at entry port 404 and flows through the detector assembly as follows: through gas flow conduit 405, vertical gas flow conduit 407, open valve 421, gas flow conduit 417, gas flow conduit 409, gas flow conduit 411, into the space above frit 463, through frit 463 and into purifier scavenger bed 408 where impurity is removed to baseline levels, through frit 464 and into gas flow conduit 413, gas flow conduit 415, passing into the space around sensor 412 and contacting the sensor, outlet port 406.

In the high point calibration mode, valve 421 is in the closed position and valve 422 is open. The gas flow stream enters the detector assembly at entry port 404 and flows through the detector assembly as follows: through gas flow conduit 405, vertical gas flow conduit 407, into the space below frit 461, through frit 461, through an impurity source bed 450 where the gas flow stream attains a known impurity concentration, through frit 462 and into the space above frit 462, down gas flow conduit 403 through check valve, through gas flow conduit 417, gas flow conduit 409, gas flow conduit 411, through open valve 422 and into gas flow conduit 413, gas flow conduit 415, passing into the space around sensor 412 and contacting the sensor, outlet port 406.

In the baseline calibration mode, the impurity is removed to a baseline or "zero-point" level by the purifier 408, which may be of the type described above for FIG. 2. The signal obtained in this mode can therefore be used to correct for any drift in baseline. The valued obtained in the high point calibration mode can likewise be used to correct for any drift in the slope of the response curve of the sensor.

The impurity source bed 450 which is used to impart a known concentration of impurity to the gas flow stream for purposes of high point calibration must be capable of rapidly equilibrating with the gas flow stream to impart to it an impurity concentration that is a known function of temperature that does not measurably change over the useful life of the in-line detector. In addition, for calibration to be useful, the impurity concentration imparted by the impurity source bed must be within the range of impurity concentrations that are being measured by the in-line detector in its normal sensing mode. The impurity source bed must be chosen in the context of the nature of the impurity being detected.

In the case of water impurity, which is key to many manufacturing processes including semiconductor device fabrication, the zeolite molecular sieves are suitable impurity source bed materials. The zeolite molecular sieves have high water capacities, in the range of tens of percents by weight, and, at temperatures of interest, are in equilibrium with suitably low vapor pressures of water. The water vapor pressures in equilibrium with zeolite molecular sieves that are loaded with known amounts of water can be found by consulting widely available tables of equilibrium isotherms. These isotherms are available over a wide range of potentially useful temperatures, e.g. from $-20°$ C. to $100°$ C. $-200°$ C. (see Davison Molecular Sieves Adsorption Equilibria, Product Literature from W. R. Grace & Co., Davison Chemical Division). Tabulated below are examples of suitable zeolite molecular sieve beds for calibration of water impurity measurement in semiconductor processing gas flow streams. Equilibrium water vapor pressures were obtained from adsorption isotherms for each zeolite at $25°$ C.

| Water Loading (wt %) Zeolite Type | 4% | 8% | 12% |
|---|---|---|---|
| | Equilibrium $H_2O$ V.P. (mm Hg at $25°$ C.) | | |
| 3A | 0.004 | 0.030 | 0.066 |
| 4A | 0.002 | 0.018 | 0.045 |
| 5A | 0.001 | 0.008 | 0.050 |

As can be seen from this table, these zeolite molecular sieve beds can provide impurity concentrations in the range of interest. In addition, the amount of water loaded into the zeolite is large compared with the amount that the zeolite would either take up from or contribute to a gas flow stream that had typical water impurity levels of 1–50 ppm. As an example, consider a gas flow stream containing 10 ppm water flowing over a 10 gram impurity source bed comprising Zeolite 4A with 8% water content by weight. The water vapor pressure in equilibrium with this bed is 0.018 mm Hg, or, at atmospheric pressure (760 mm Hg), 23 ppm. If 30 liters of gas passes over this Zeolite 4A and rapidly equilibrates with it, the amount of water lost from the zeolite would be $\leq 3 \times 10^{-4}$ g, a very small amount compared with the 0.8 grams of water originally present.

If, on the other hand, 30 liters of a gas flow stream containing 40 ppm water impurity flowed over and rapidly equilibrated with the same zeolite bed, the amount of water added to the zeolite would be $>0.4 \times 10^{-3}$ gram. Thus the ability of the zeolite to provide a constant impurity level to the gas flow stream for purposes of calibration would not be affected by contact with the gas flow stream if the gas flow stream contained impurity in the same approximate concentration range.

Figure 5:
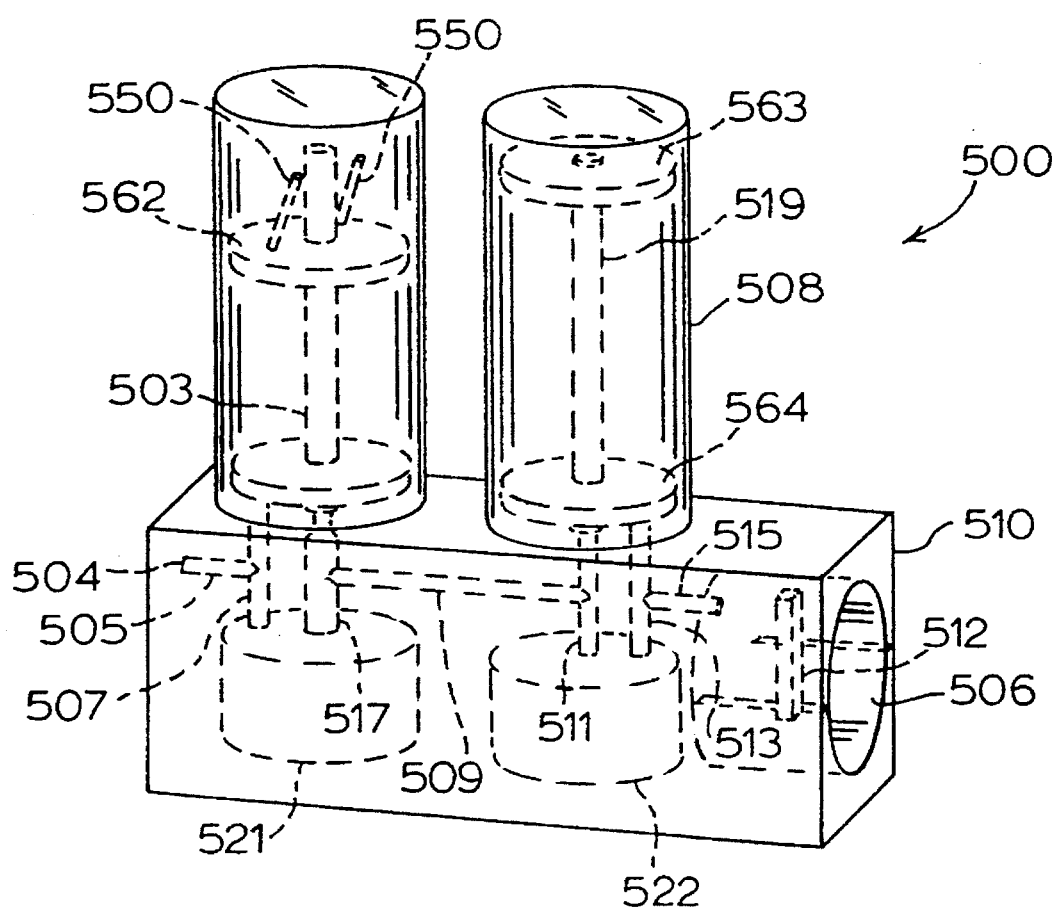
FIG. 5 is a perspective view of a detector that may be periodically recalibrated at many concentrations, a baseline concentration and many well-characterized, non-zero values of impurity concentration in a flowing gas stream, having a means for calibration at the low, baseline impurity concentration and at the higher well-characterized impurity concentrations.

FIG. 5 is a schematic representation of a detector system 500 according to another embodiment of the present invention, similar to the detector system of FIG. 4, and wherein all parts and elements corresponding to the system previously shown and described with reference to FIG. 4 are correspondingly numbered, but by addition of 100 to the reference numeral of the corresponding reference number of the same or similar part or element in FIG. 4. This embodiment provides calibration of the sensor baseline and calibration of the detector sensitivity at multiple known impurity concentration points, provided that a mass flow controller or other flow control device provides controllable and measurable gas stream flow rate. The ability to calibrate at multiple impurity concentrations is desirable because the response curves of many highly sensitive sensor elements are not linear. In addition, the in-line detector may then be accurately calibrated in more than one impurity concentration regime to suit changing conditions.

The detector system in FIG. 5 operates similarly to that of FIG. 4, with the key difference that instead of providing an impurity source bed that imparts one known impurity concentration to the gas flow stream, the detector system of FIG. 5 includes an impurity source such as one or more permeation tube(s) 550 that, at a constant temperature, provides impurity at a constant rate. Thus the impurity concentration in the gas flow stream may be controlled by varying the gas stream flow rate.

Surface acoustic wave (SAW) devices may be employed in the detector systems shown in FIGS. 4 and 5. SAW devices are usefully employed as chemical sensors in the broad practice of the present invention, due to their ability to respond to changes caused by the binding of atoms and molecules to the SAW device surfaces which lie in the path of the transmitted acoustic wave. The response of the SAW device can take either the form of a surface wave amplitude attenuation, or, more commonly, the form of a change in the wave velocity. These changes, in turn, result from the formation of a thick surface layer of bound material (in the case of SAW devices used in the present invention, a layer of the impurity species bound to the affinity substrate), which differs from the SAW substrate lacking such bound impurity species, in terms of elasticity, mass density, viscosity, and/or conductivity.

SAW devices can be applied as gas sensors, as well as for sensing of liquid deposited on the SAW affinity surface. For gas sensing operations, a Rayleigh mode acoustic wave normally is employed; for liquid phase sensing, various acoustic wave modalities may be employed, including the Rayleigh mode, horizontal shear plate mode, or flat plate mode acoustic waves. In the broad practice of the present invention, for gas impurity sensing, Rayleigh mode SAW gas sensors are preferably employed. Rayleigh mode waves yield the highest mass response sensitivity and are the operating mode of choice for gas sensing applications where wave attenuation is not a problem.

The high sensitivity of SAW devices in gas impurity sensing applications is well known and established in the art, and various reports have been published demonstrating the utility of SAW devices in specific impurity-containing gas systems. For example, Vetelino, J. F., et al, IEEE Trans. Ultrason., Ferroelec. Freq. Control, UFFC-34(2), 156–161 (1987) describes the use of a SAW device having a surface coating of $WO_3$ as employed for sensing of hydrogen sulfide, with sensitivity to concentrations of hydrogen sulfide of less than 10 ppm. Venema, A., et al, IEEE Trans. Ultrason., Ferroelec. Freq. Control, UFFC-34(2), 148–155 (1987) reports the use of a coating of copper phthalocyanine, an organic semiconductor, on a SAW device to sense nitrogen dioxide ($NO_2$) with a threshold detection sensitivity of 500 Vui. Both of these reported applications involve the use of dual SAW device configurations to compensate for non-specific effects.

With reference to the specific impurity species-binding coating which may be employed in a SAW device sensor element in the detector systems of FIGS. 4 or 5, an acceptable coating must meet the following criteria:
(1) the coating must reversibly bind the impurity species in a suitable concentration range of interest (e.g., water in a 10–100 ppb range);
(2) the coating must bind the impurity in the presence of the reactive gases of interest, with a minimum of interference from the process gas stream;
(3) the coating must be non-contaminating with respect to the gas streams of interest;
(4) the coating must be stable over an extended period of time; and
(5) the coating must be easily and reproducibly applied to the sensing surface of the SAW device.

Even when considering a single impurity species such as water, it is apparent that no universal hygroscopic coating exists for all possible gas streams of interest which may contain such (water) impurity. In the case of water as an impurity, it is expected that inert gases and hydride gases of Group IV—VI elements of the Periodic Table will be able to use the same moisture-affinity coating. The impurity-affinity coating employed for sensing of water impurity in hydrogen halide gases, however, will be different.

In the case of inert and hydride reactive gases (including those of Group IV—VI elements), a poly(vinylamine) coating may potentially usefully be employed in the broad practice of the present invention, provided that such coating meets the criteria (1)–(5) stated above. Amines are know to reversibly bind water, and, in fact, an amine coating is employed in the aforementioned DuPont 5700 Moisture Analyzer which, as noted, has a sensitivity in the 10 ppb range, and has been employed successfully in inert gas as well as arsine moisture-sensing service.

The molecular weight of the poly(vinylamine) is desirably high enough so that the polymer will have no appreciable vapor pressure which would otherwise contaminate the gas stream being monitored for impurity concentration. The poly(vinylamine) polymer is non-degradable in hydride gas streams, so that such polymer is non-contaminating in the gas streams being monitored.

In addition, poly(vinylamine)s are soluble in polar solvents, so that they are readily applied to SAW device surfaces, e.g., by spin-coating of polar solvent solutions of such polymers. Suitable poly(vinylamine)s are commercially available from Polysciences, Inc. (Warrington, Pa.) and may be usefully employed in as-purchased form, for dissolution into polar solvents and application to the sensor surface by suitable application techniques such as spin coating.

When moisture is the critical impurity to be sensed in hydrogen halide gas streams, a suitable coating material for the SAW device affinity surface comprises poly(vinylsulfonic acid). This material is the acid equivalent to the poly(vinylamine) coating discussed above, and is usefully employable for affinity surface coatings on SAW devices in hydride gas service. Poly(vinylsulfonic acid) is commercially available from Polysciences, Inc. and may be employed in as-furnished form by dissolution into a suitable solvent, and application, e.g., by spin coating, to the sensing surface of the SAW device.

The aforementioned illustrative polymeric materials employed to coat the sensor surface of the SAW device may be spun coated by aqueous solutions thereof.

After the SAW device is coated with the impurity-affinity layer or film, the detection capability thereof may be tested using calibrated standards such as the calibration device 600 shown and described with reference to FIG. 6 above. In the course of such calibration testing, the response of the coating is measured, and the coating is modified if necessary to achieve the desired highly sensitive, stable, and reproducible sensor layer required in the detection system of the present invention.

Figure 6:
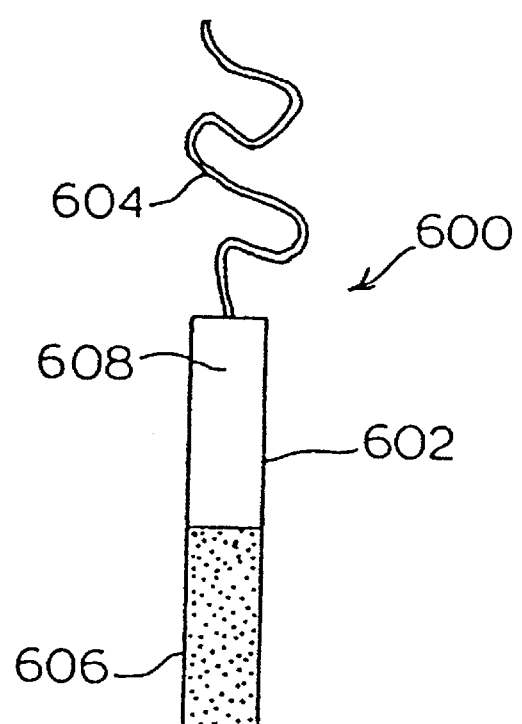
FIG. 6 is a schematic representation of a permeation tube device which may be used as a calibration standard for gas impurity sensors employed in the practice of the present invention.

FIG. 6 is a schematic representation of an impurity standard calibration device 600 as may be used in the practice of the present invention, for example as impurity source 550 in FIG. 5. As shown in FIG. 6, the calibration device 600 comprises a container 602 having disposed therein an impurity constituent liquid 606. Above this impurity liquid is a vapor space 608 in vapor flow communication with a permeation tube 604, which is formed of a permeable membrane material which allows the out-diffusion of the impurity species into the gas surrounding the permeation tube. The permeation tube may be formed of a suitable polymeric material having known and controllable permeability characteristics, e.g., polytetrafluoroethylene, or other suitable polymeric or, alternatively, nonpolymeric material.

Consistent with the criticality of water as an impurity species in semiconductor manufacturing operations, the calibration device 600 shown in FIG. 6 may suitably contain as the liquid 606 a quantity of water. With the homogeneous structure of the permeation tube 604, the diffusion of permeant (water) at constant temperature will also be constant.

The water vapor diffusing out of the permeation tube, through the surface along its length, then may be passed into a carrier gas, e.g., a previously purified gas stream (with respect to impurity therein), to provide a constant, known concentration of impurity for calibration of the SAW device or other sensor element in the practice of the present invention. The calibration device 600 shown in FIG. 6 affords a simple, and highly reducible, means for supplying known impurity levels at sub-ppm concentrations.

The permeation tube 604 of the calibration device may itself be calibrated either gravimetrically or by measuring the water level of the liquid 606 in container 602, using a commercially available trace moisture analyzer, such as for example a DuPont 5700 Moisture Analyzer, available from E. I. DuPont de Nemours and Company (Wilmington, Del.), which is capable of detecting moisture levels as low as 10 ppb.

Figure 7:
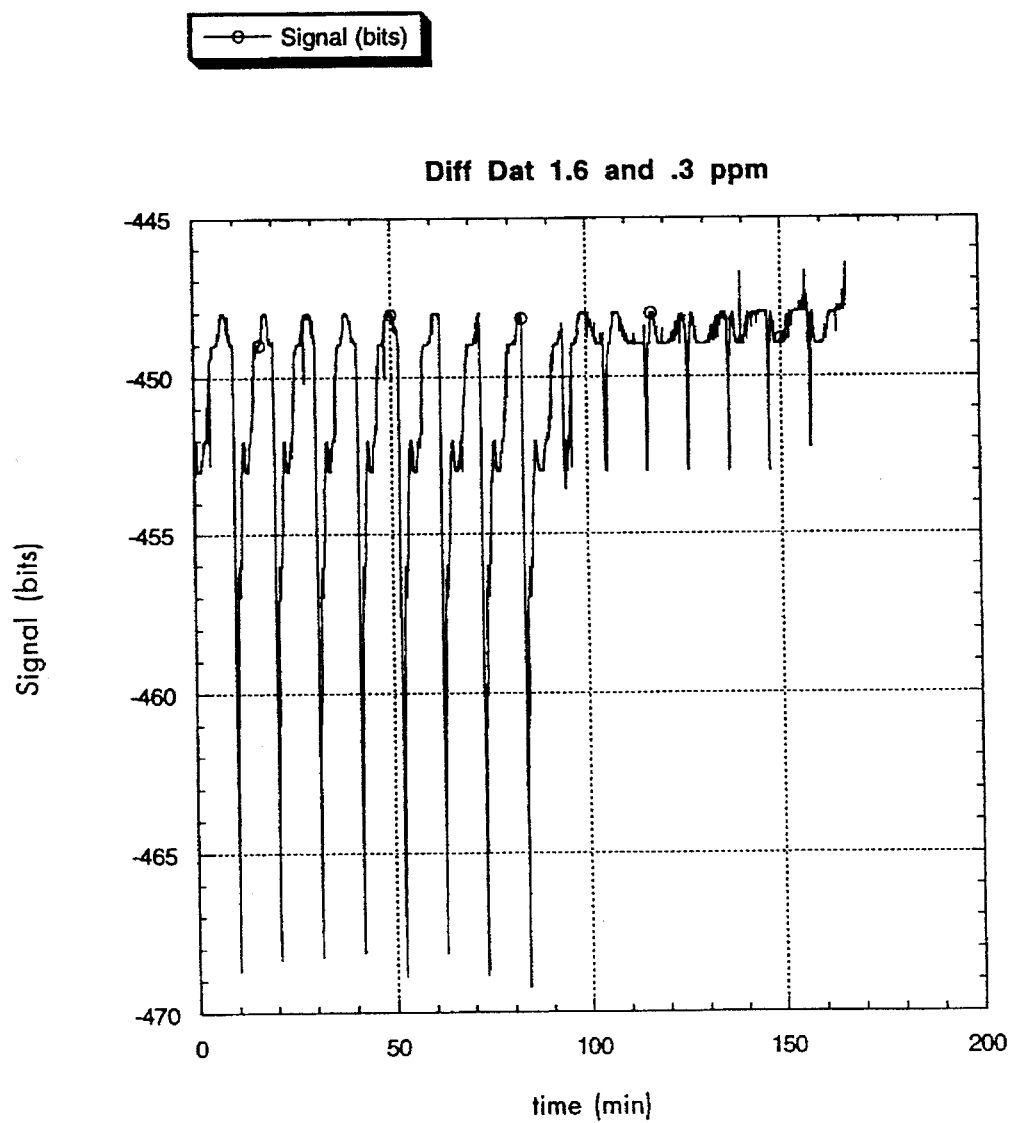
FIG. 7 shows the output signal versus time for a hygrometer sensor exposed to 1.6 ppm moisture in a 2 liter per minute inert gas stream alternately with a purified ("zero") 2 liter per minute inert gas stream, and then to 0.3 ppm moisture in a 2 liter per minute inert gas stream alternately with the zero gas stream.

FIG. 7 shows output signal versus time for a hygrometer sensor exposed to high and low concentrations of moisture in an inert gas stream. The data of the front end were collected using a 12-bit a/d converter. Data collected were plotted as bits with no linearization. The hygrometer was exposed to 1.6 ppm moisture and 0.3 ppm moisture in a 2 liter per minute inert gas stream. The bypass valve was cycled to provide 30 seconds sample gas and 10 minutes zero gas. A change in the signal of about 20 bits was observed upon 30 second exposure to 1.6 ppm moisture. Upon 30 second exposure to 300 ppb moisture, about 4 bits of change were observed. For this sensor and contaminant, the limit of this technique may be about 300 ppb. There were only small changes in the signal below this level.

The switch between 1.6 and 0.3 ppm took place at about 90 minutes. The break in data was very clean. There was no blurring of data between the two concentrations.

Figure 8:
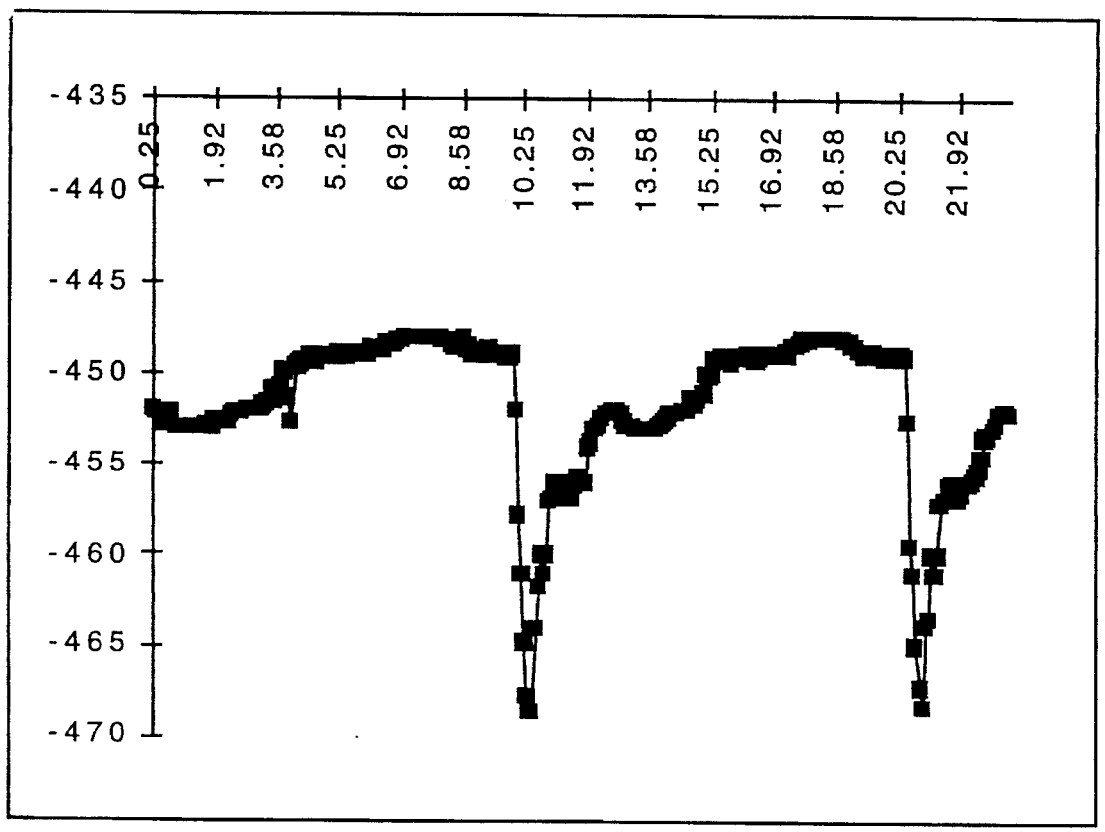
FIG. 8 shows a close-up of the data from FIG. 7, for two cycles at the 1.6 ppm moisture level.

The data for two cycles are shown in FIG. 8 at the 1.6 ppm moisture level. This close-up of the data shows repeatable structure to the changes in signal. At this time, the source and significance of the secondary structure is not known.

Under the conditions of the test, the sensor had recovered to the baseline noise within a range of 5 to 6 minutes. This recovery time is to be compared with a recovery time of several hours to recover from static equilibrium with a gas stream containing ppm levels of moisture.

Figure 9:
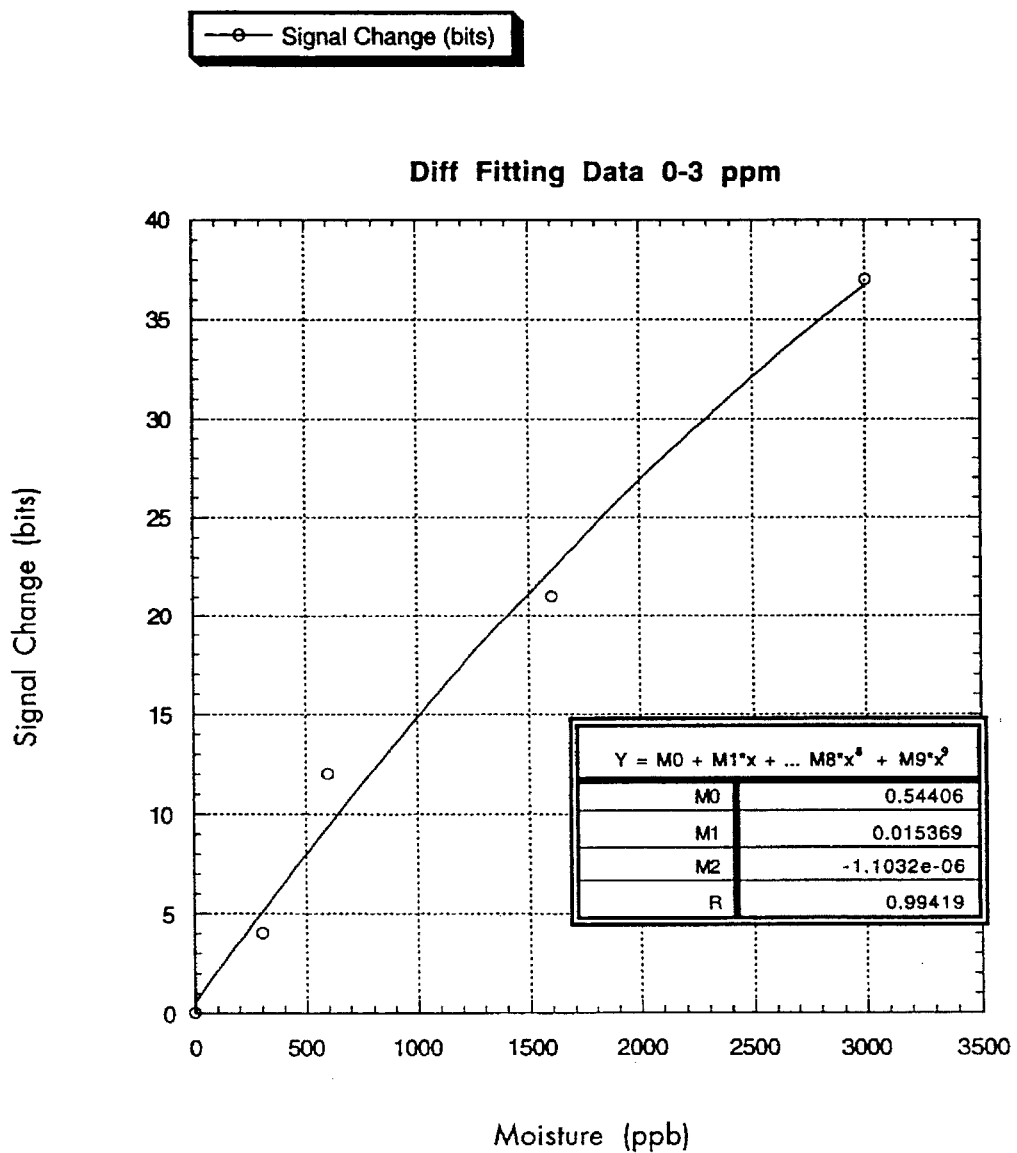
FIG. 9 shows a calibration curve for a hygrometer sensor, made over the range of 300 to 3000 ppb, by which the change in signal can be extrapolated to the equilibrium concentration.

As mentioned before, the change in signal can be extrapolated to the equilibrium concentration. A calibration curve was made over the range of 300 to 3000 ppb. The curve is shown in FIG. 9, which shows signal change (bits) versus ppb moisture, for 30 second exposures to the sample gas stream. The data appear to be roughly linear. However, a slightly better fit is obtained with a second order polynomial equation. The quadratic term is quite small.

Calibrations may be carried out up to the 20 ppm range in the differential mode, for this sensor/contaminant system. These experiments demonstrate that the differential mode offers a fast response from the in-line monitor in high moisture conditions, without sacrificing the sensitivity capabilities of the detector. Instead of the multi-hour times that are required for recovery when operating in the normal mode, when operating in the differential mode, recovery times are in the 5–10 minute range. This time can be reduced further without significant difficulties.

The crossover between operation in the normal mode and in the differential mode may be manual or automatic. In most cases, the in-line monitor is in normal mode for most of its operations. A central processing unit (CPU), which may as previously described comprise any suitable calculational means, collects the signal and calculates an average value and standard deviation $\sigma$, a measure of the noise in the signal. If the CPU detects a change in signal greater than a predetermined amount, for example $5\sigma$, the CPU resets the in-line monitor to operation in the differential mode. In the differential mode, the in-line monitor takes brief snapshots of the moisture level. A calibration curve designed for the differential mode is used. When the high moisture level has dropped off, the CPU switches the in-line monitor back to operation in the normal mode, where greater low level moisture sensitivity is found.

While the preceding description has been directed primarily to in-line monitoring systems and methods utilizing sensor media of a reversibly sorptive character, i.e. physical sorbents or other reversible impurity species binding media, it will be recognized that the utility of the invention is not thus limited. The invention also contemplates the use of chemisorbent sensor media, e.g., chemical getters, in which the impurity species binding is irreversible, by virtue of chemical reaction or very high binding affinity constants. In such instances, the invention may utilize the sensor in a differential mode of sensing of gas containing impurity species, to prolong the useful life of the sensor medium beyond what would otherwise be possible in the use of such affinity material.

For example, the sensor may comprise a chemical getter material such as a metal or metal alloy, e.g., elemental barium, which binds reactively and irreversibly to gas impurity species such as oxygen, nitrogen, hydrogen, etc:

Various other features, aspects, and embodiments of the invention are described in my prior co-pending U.S. application Ser. No. 07/930,184 filed Aug. 17, 1992, now U.S. Pat. No. 5,825,705, which was a continuation-in-part of my prior co-pending U.S. patent application Ser. No. 07/628,490, filed Dec. 14, 1990, and issued Aug. 18, 1992 as U.S. Pat. No. 5,138,869, the disclosures of which hereby are incorporated herein by reference in their entirety, to the extent not otherwise present herein.

Although the invention has been described with respect to particular features, aspects, and embodiments thereof, it will be apparent that numerous variations, modifications, and other embodiments are possible within the broad scope of the present invention, and accordingly all variations, modifications, and embodiments are to be regarded as being within the spirit and scope of the invention.

What is claimed is:

1. An in-line monitoring system for determining the calibrated concentration of an impurity species in a flowing gas stream, in a low concentration range below a predetermined concentration value, and in a high concentration range above said predetermined concentration value, said system comprising:

(a) means defining a flow path for a flowing gas stream;

(b) a gas purifier through which gas deriving from the flowing gas stream is flowable to remove impurity species therefrom;

(c) means for sensing the impurity species concentration of gas deriving from the flowing gas stream;

(d) means for selectively flowing gas from the flow path through the gas purifier to yield purified gas depleted in said impurity species;

(e) means for flowing purified gas from said gas purifier to said sensing means;

(f) means for selectively flowing gas from the flow path to the sensing means without passage of the gas through the gas purifier;

(g) means operatively coupled to said sensing means for determining a calibrated equilibrium value of impurity species concentration in the flowing gas stream from impurity species concentration in unpurified gas sensed by said sensing means in calibrative relationship to impurity species concentration of purified gas sensed by said sensing means;

(h) flow control means operatively coupled with gas flow means (f) and (g), and arranged to selectively, alternatively and repetitively flow gas deriving from the flowing gas stream through gas flowing means (f) to the gas purifier for a first selected period of time $t_1$, and subsequently through gas flowing means (g) for a second selected period of time $t_2$, in a repeating cycle, wherein in the low concentration range below said predetermined concentration value, $t_2 > t_1$, and wherein in the high concentration range above said predetermined concentration value, $t_1 > t_2$.

2. An in-line monitoring system according to claim 1, wherein in the low concentration range below said predetermined concentration value, $0.50 < t_2/(t_1+t_2) \leq 0.99$, and wherein in the high concentration range above said predetermined concentration value, $0.5 < t_1/(t_1+t_2) \leq 0.99$.

3. An in-line monitoring system according to claim 1, wherein the sensor means (c) comprise physical sorption sensor means, and wherein in the high concentration range above said pre-determined concentration value, the second selected period of time $t_2$ is selected to allow dynamic contact equilibrium to occur but not static equilibrium.

4. An in-line monitoring system according to claim 1, wherein the sensing means (c) comprise a physical sorption medium having sorptive affinity for the impurity species.

5. An in-line monitoring system according to claim 1, wherein the gas purifier comprises a chemisorbent material which is chemically reactive with the impurity species to remove same from the gas deriving from the flowing gas stream.

6. An in-line monitoring system according to claim 1, wherein the sensing means (c) comprise a hygrometric sensor.

7. An in-line monitoring system according to claim 1, wherein the means (g) for determining a calibrated equilibrium value of impurity species concentration in the flowing gas stream from impurity species concentration in unpurified gas sensed by said sensing means in calibrated relationship to impurity species concentration of purified gas sensed by said sensing means, comprises a digital computer.

8. An in-line monitoring system according to claim 1, wherein the means (g) for determining a calibrated equilibrium value of impurity species concentration in the flowing gas stream from impurity species concentration in unpurified gas sensed by said sensing means in calibrated relationship to impurity species concentration of purified gas sensed by said sensing means, comprises a microprocessor.

9. An in-line monitoring system according to claim 1, wherein the flow control means (h) comprise an automatic valve operatively coupled with gas flowing means (f) and (g).

10. A method for determining the calibrated concentration of an impurity species in a flowing gas stream, in a low concentration range below a predetermined concentration value, and in a high concentration range above said predetermined concentration value, said method comprising:

providing an in-line monitoring system comprising:

(a) means defining a flow path for a flowing gas stream;

(b) a gas purifier through which gas deriving from the flowing gas stream is flowable to remove impurity species therefrom;

(c) means for sensing the impurity species concentration of gas deriving from the flowing gas stream;

(d) means for selectively flowing gas from the flow path through the gas purifier to yield purified gas depleted in said impurity species;

(e) means for flowing purified gas from said gas purifier to said sensing means;

(f) means for selectively flowing gas from the flow path to the sensing means without passage of the gas through the gas purifier;

(g) means operatively coupled to said sensing means for determining a calibrated equilibrium value of impurity species concentration in the flowing gas stream from impurity species concentration in unpurified gas sensed by said sensing means in calibrative relationship to impurity species concentration of purified gas sensed by said sensing means;

(h) flow control means operatively coupled with gas flowing means (f) and (g), and arranged to selectively, alternatively and repetitively flow gas deriving from the flowing gas stream through gas flowing means (f) to the gas purifier for a first selected period of time $t_1$, and subsequently through gas flowing means (g) for a second selected period of time $t_2$, in a repeating cycle, wherein in the low concentration range below said predetermined concentration value, $t_2 > t_1$, and wherein in the high concentration range above said predetermined concentration value, $t_1 > t_2$;

flowing gas from the flowing gas stream selectively from the flow path through the gas purifier to yield purified gas depleted in said impurity species, alternatingly with flowing gas from the flow path through the gas flowing means (f), and passing the gas to said sensing means; and selectively operating said flow control means (h) to flow gas through means (f) to the gas purifier for a first selected period of time $t_1$, and subsequently through gas flowing means (g) for a second period of time $t_2$, in a repeating cycle, wherein in the low concentration range below said predetermined concentration value, $t_2 > t_1$, and wherein in the high concentration range above said predetermined concentration value, $t_1 > t_2$.

11. A method according to claim 10, wherein in the low concentration range below said predetermined concentration value, $0.50 < t_2/(t_1+t_2) \leq 0.99$.

12. A method according to claim 10, wherein the sensing means comprises a physical sorption sensor, and wherein in the high concentration above said predetermined concentration value, the second selected period of time $t_2$ is selected to allow dynamic contact equilibrium to occur but not static equilibrium.

13. A method according to claim 10, wherein the sensing means (c) comprise a physical sorption medium having sorptive affinity for the impurity species.

14. A method according to claim 10, wherein the gas purifier comprises a chemisorbent material which is chemically reactive with the impurity species to remove same from the gas deriving from the flowing gas stream.

15. A method according to claim 10, wherein the sensing means (c) comprise a hygrometric sensor.

16. A method according to claim 10, wherein the means (g) for determining a calibrated equilibrium value of impurity species concentration in the flowing gas stream from impurity species concentration in unpurified gas sensed by said sensing means in calibrated relationship to impurity species concentration of purified gas sensed by said sensing means, comprises a digital computer.

17. A method according to claim 10, wherein the means (g) for determining a calibrated equilibrium value of impurity species concentration in the flowing gas stream from impurity species concentration in unpurified gas sensed by said sensing means in calibrated relationship to impurity species concentration of purified gas sensed by said sensing means, comprises a microprocessor.

18. A method according to claim 10, wherein the flow control means (h) comprise an automatic valve operatively coupled with gas flowing means (f) and (g).

19. A method of determining a calibrated concentration of an impurity species in a flowing gas stream, in a low concentration range below a predetermined concentration value, and in a high concentration range above said predetermined concentration value, said method comprising:

sensing the impurity species concentration of gas derived from the gas flow stream in a sequential and repetitive sensing operation wherein in a first sensing mode the gas is purified of impurity species prior to sensing thereof and wherein in a second sensing mode the gas is unpurified, and wherein in the first sensing mode and second sensing mode, the sensing mode cycle times are varied in accordance with the impurity species concentration, so that in said low concentration range below said predetermined concentration value, the second sensing mode cycle time is greater than the first sensing mode cycle time, and wherein in said high concentration range above said predetermined concentration value, said first sensing mode cycle time is greater than the second sensing mode cycle time; and determining a calibrated equilibrium value of impurity species concentration in the flowing gas stream from sensing concentrations in the first and second sensing modes.

20. An in-line monitoring system for determining a calibrated concentration of an impurity species in a flowing gas stream, in a low concentration range below a predetermined concentration value, and in a high concentration range above said predetermined concentration value, said system comprising:

a purifier for removing impurity species from gas derived from the flowing gas stream;

a means for sensing the impurity species concentration of gas derived from the gas flow stream in a sequential and repetitive sensing operation wherein in a first sensing mode the gas is purified of impurity species by passage thereof through said purifier prior to sensing thereof and wherein in a second sensing mode the gas in unpurified, and wherein in the first sensing mode and second sensing mode, the sensing mode cycle times are varied in accordance with the impurity species concentration, so that in said low concentration range below said predetermined concentration value, the second sensing mode cycle time is greater than the first sensing mode cycle time, and wherein in said high concentration range above said predetermined concentration value, said first sensing mode cycle time is greater than the second sensing mode cycle time, and a means for determining a calibrated equilibrium value of impurity species concentration in the flowing gas stream from sensing concentrations in the first and second sensing modes.

21. A method of determining a calibrated concentration of impurity species in a flowing gas stream, wherein gas derived from the gas flow stream is alternatingly sensed as to its impurity species concentration in purified and unpurified conditions, and said sensing comprises contacting of gas with a sensor including a binding medium having irreversible binding affinity for the impurity species, said method comprising sensing impurity species concentration of unpurified gas by said sensor in a differential mode, and controlling (1) sensing time of the sensor in exposure to said unpurified gas, relative to (2) sensing time of the sensor in exposure to purified gas, in response to impurity species concentration of unpurified gas sensed by said sensor, wherein sensing time of the sensor in exposure to said unpurified gas is less than 50% of the operating time of the sensor, whereby the sensor service life is extended relative to continuous sensing of unpurified gas.

22. An in-line monitoring system for determining a calibrated concentration of impurity species in a flowing gas stream, comprising:

a sensor including a binding medium having irreversible binding affinity for the impurity species, for sensing impurity species concentration in a gas;

means for purifying gas derived from said flowing gas stream to yield purified gas;

means for flowing unpurified gas derived from said flowing gas stream to said sensor and for flowing purified gas from said gas purifying means to said sensor, such that said unpurified gas is sensed by said sensor in a differential mode wherein sensing time of the sensor in exposure to said unpurified gas is less than 50% of the operating time of the sensor, whereby the sensor service life is extended relative to continuous sensing of unpurified gas;

means for determining a calibrated concentration of impurity species in said flowing gas stream from impurity species concentrations of said purified and unpurified gas sensed by said sensor; and means for controlling (1) sensing time of the sensor in exposure to said unpurified gas, relative to (2) sensing time of the sensor in exposure to purified gas, in response to impurity species concentration of unpurified gas sensed by said sensor.

* * * * *

UNITED STATES PATENT AND TRADEMARK OFFICE
CERTIFICATE OF CORRECTION

PATENT NO. : 5,583,282
DATED : December 10, 1996
INVENTOR(S) : Glenn M. Tom

It is certified that error appears in the above-indentified patent and that said Letters Patent is hereby corrected as shown below:

Column 20, Line 7,      "Water Loading (wt%)" should be on the same line as the percentages in the table Column 20, Line 33,      ">$0.4 \times 10^{-3}$" should be --$\leq 0.4 \times 10^{-3}$--

Signed and Sealed this

Tenth Day of June, 1997

Attest:

BRUCE LEHMAN

*Attesting Officer*      *Commissioner of Patents and Trademarks*